United States Patent
Kirchhoff et al.

(10) Patent No.: US 8,071,720 B2
(45) Date of Patent: Dec. 6, 2011

(54) **RECOMBINANT POLYPEPTIDES FOR DIAGNOSING INFECTION WITH *TRYPANOSOMA CRUZI***

(76) Inventors: Louis V Kirchhoff, Iowa City, IA (US); Keiko Otsu, Iowa City, IA (US)

( * ) Notice: Subject to any disclaimer, the term of this patent is extended or adjusted under 35 U.S.C. 154(b) by 0 days.

(21) Appl. No.: 13/022,493

(22) Filed: Feb. 7, 2011

(65) Prior Publication Data

US 2011/0171751 A1     Jul. 14, 2011

Related U.S. Application Data

(62) Division of application No. 12/355,338, filed on Jan. 16, 2009, now abandoned, which is a division of application No. 10/726,692, filed on Dec. 4, 2003, now Pat. No. 7,491,515.

(60) Provisional application No. 60/430,654, filed on Dec. 4, 2002.

(51) Int. Cl.
    *C07K 1/00*     (2006.01)
    *G01N 33/53*     (2006.01)

(52) U.S. Cl. .......................... 530/350; 435/7.1; 435/975

(58) Field of Classification Search .................. None
See application file for complete search history.

(56) References Cited

U.S. PATENT DOCUMENTS 5,916,572 A * 6/1999 Reed et al. ................. 424/269.1

* cited by examiner

*Primary Examiner* — Albert Navarro

(57) ABSTRACT

Recombinant polypeptides are disclosed that are useful for diagnosing American trypanosomiasis, or Chagas disease, a disease caused by the infectious agent *Trypanosoma cruzi*. Preferably, DNA sequences encoding the recombinant proteins are placed in plasmid vectors to be expressed in an organism.

12 Claims, 2 Drawing Sheets

Fig. 1 (Ag15) 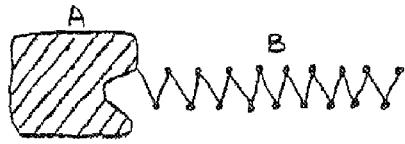
Fig. 1a (FP3) 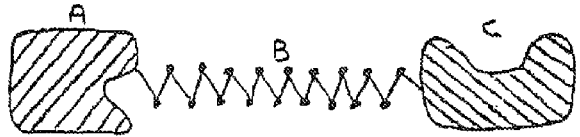
Fig. 1b (FP4) 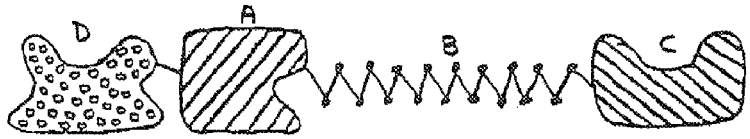
Fig. 1c (FP5) 
Fig. 1d (FP6) 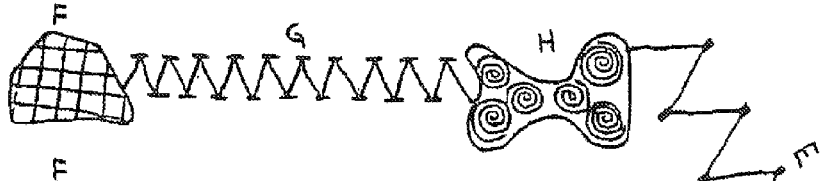
Fig. 1e (FP7) 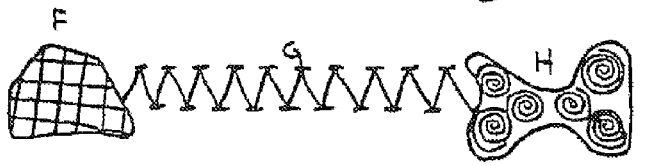
Fig. 1f (FP8) 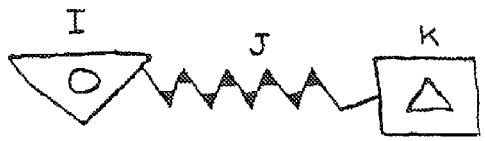
Fig. 1g (FP9) 
Fig. 1h (FP10) 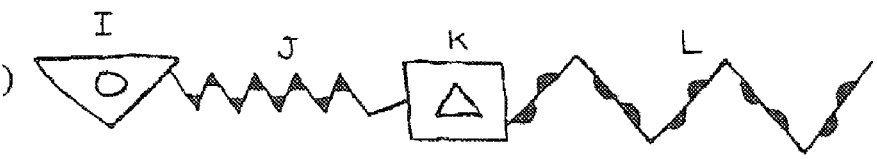

SEQUENCE LISTING

<160> NUMBER OF SEQ ID NOS: 57

<210> SEQ ID NO 1
<211> LENGTH: 1521
<212> TYPE: DNA
<213> ORGANISM: Trypanosoma cruzi
<220> FEATURE:
<221> NAME/KEY: CDS
<222> LOCATION: (1)..(21)
<220> FEATURE:
<221> NAME/KEY: CDS
<222> LOCATION: (25)..(162)
<220> FEATURE:
<221> NAME/KEY: CDS
<222> LOCATION: (166)..(273)
<220> FEATURE:
<221> NAME/KEY: CDS
<222> LOCATION: (277)..(330)
<220> FEATURE:
<221> NAME/KEY: CDS
<222> LOCATION: (334)..(429)
<220> FEATURE:
<221> NAME/KEY: CDS
<222> LOCATION: (433)..(573)
<220> FEATURE:
<221> NAME/KEY: CDS
<222> LOCATION: (628)..(678)
<220> FEATURE:
<221> NAME/KEY: CDS
<222> LOCATION: (691)..(759)
<220> FEATURE:
<221> NAME/KEY: CDS
<222> LOCATION: (763)..(834)
<220> FEATURE:
<221> NAME/KEY: CDS
<222> LOCATION: (838)..(861)
<220> FEATURE:
<221> NAME/KEY: CDS
<222> LOCATION: (865)..(876)
<220> FEATURE:
<221> NAME/KEY: CDS
<222> LOCATION: (880)..(897)
<220> FEATURE:
<221> NAME/KEY: CDS
<222> LOCATION: (901)..(918)
<220> FEATURE:
<221> NAME/KEY: CDS
<222> LOCATION: (922)..(933)
<220> FEATURE:
<221> NAME/KEY: CDS
<222> LOCATION: (937)..(948)
<220> FEATURE:
<221> NAME/KEY: CDS
<222> LOCATION: (952)..(975)
<220> FEATURE:
<221> NAME/KEY: CDS
<222> LOCATION: (979)..(1017)
<220> FEATURE:
<221> NAME/KEY: CDS
<222> LOCATION: (1021)..(1059)
<220> FEATURE:
<221> NAME/KEY: CDS
<222> LOCATION: (1063)..(1101)
<220> FEATURE:
<221> NAME/KEY: CDS
<222> LOCATION: (1105)..(1143)
<220> FEATURE:
<221> NAME/KEY: CDS
<222> LOCATION: (1147)..(1185)
<220> FEATURE:
<221> NAME/KEY: CDS
<222> LOCATION: (1189)..(1227)
<220> FEATURE:
<221> NAME/KEY: CDS
<222> LOCATION: (1231)..(1269)
<220> FEATURE:
<221> NAME/KEY: CDS

```
<222> LOCATION: (1273)..(1311)
<220> FEATURE:
<221> NAME/KEY: CDS
<222> LOCATION: (1315)..(1353)
<220> FEATURE:
<221> NAME/KEY: CDS
<222> LOCATION: (1357)..(1395)
<220> FEATURE:
<221> NAME/KEY: CDS
<222> LOCATION: (1399)..(1437)
<220> FEATURE:
<221> NAME/KEY: CDS
<222> LOCATION: (1441)..(1479)
<220> FEATURE:
<221> NAME/KEY: CDS
<222> LOCATION: (1483)..(1521)
<220> FEATURE:
<221> NAME/KEY: CDS
<222> LOCATION: (577)..(624)
<220> FEATURE:
<221> NAME/KEY: CDS
<222> LOCATION: (682)..(687)

<400> SEQUENCE: 1
```

| | | | | | | | | | | | | | | | | |
|---|---|---|---|---|---|---|---|---|---|---|---|---|---|---|---|---|
| tat | ggc | ccg | agc | tgt | ggt | gct | tga | gga | tgg | agc | gct | tta | cgt | ggc | gga | 48 |
| Tyr | Gly | Pro | Ser | Cys | Gly | Ala | | Gly | Trp | Ser | Ala | Leu | Arg | Gly | Gly | |
| 1 | | | 5 | | | | | | 10 | | | | | 15 | | |
| caa | tgc | caa | caa | cct | cgt | tcg | aga | aat | ctc | caa | tgg | cgt | tgt | cac | ttc | 96 |
| Gln | Cys | Gln | Gln | Pro | Arg | Ser | Arg | Asn | Leu | Gln | Trp | Arg | Cys | His | Phe | |
| | | | 20 | | | | | 25 | | | | | 30 | | | |
| gtt | tat | tac | gga | agg | act | gct | ggg | ccc | atc | gta | cat | caa | acc | gta | cag | 144 |
| Val | Tyr | Tyr | Gly | Arg | Thr | Ala | Gly | Pro | Ile | Val | His | Gln | Thr | Val | Gln | |
| | | 35 | | | | | 40 | | | | | 45 | | | | |
| ccg | tac | aaa | tgg | cgc | tca | tga | ctt | gtt | tgt | gtc | gga | cac | ggg | caa | atc | 192 |
| Pro | Tyr | Lys | Trp | Arg | Ser | | Leu | Val | Cys | Val | Gly | His | Gly | Gln | Ile | |
| | 50 | | | | | | 55 | | | | | 60 | | | | |
| acg | cat | cat | ttt | tgc | ccc | acc | tca | gaa | aaa | aac | gtt | cat | cac | agt | gtt | 240 |
| Thr | His | His | Phe | Cys | Pro | Thr | Ser | Glu | Lys | Asn | Val | His | His | Ser | Val | |
| | 65 | | | | | 70 | | | | | 75 | | | | | |
| tat | aac | agg | att | cca | gcc | gga | tgt | tct | tca | aat | tag | cga | gaa | gag | tcg | 288 |
| Tyr | Asn | Arg | Ile | Pro | Ala | Gly | Cys | Ser | Ser | Asn | | Arg | Glu | Glu | Ser | |
| 80 | | | | | 85 | | | | | | | 90 | | | | |
| ttt | gat | gtt | tgc | cat | ctg | caa | ttc | cac | gaa | aat | tct | tgc | gat | taa | tat | 336 |
| Phe | Asp | Val | Cys | His | Leu | Gln | Phe | His | Glu | Asn | Ser | Cys | Asp | | Tyr | |
| | 95 | | | | | 100 | | | | | 105 | | | | | |
| gca | ggg | agc | cac | aac | ccc | gaa | gga | gta | ctg | gca | agt | tgg | aaa | tgc | gga | 384 |
| Ala | Gly | Ser | His | Asn | Pro | Glu | Gly | Val | Leu | Ala | Ser | Trp | Lys | Cys | Gly | |
| | 110 | | | | | 115 | | | | | 120 | | | | | |
| ctg | cat | ggg | cta | tca | gag | ttc | cct | cat | gct | cac | gac | cga | gga | gga | taa | 432 |
| Leu | His | Gly | Leu | Ser | Glu | Phe | Pro | His | Ala | His | Asp | Arg | Gly | Gly | | |
| 125 | | | | | 130 | | | | | 135 | | | | | | |
| act | cct | cta | cta | cgg | cat | att | aaa | tgg | aac | ccc | atc | cat | cat | gtc | ttt | 480 |
| Thr | Pro | Leu | Leu | Arg | His | Ile | Lys | Trp | Asn | Pro | Ile | His | His | Val | Phe | |
| 140 | | | | | 145 | | | | | 150 | | | | | 155 | |
| acc | cgc | cac | caa | aac | gaa | gac | gga | agc | acc | cag | aat | ttg | ccc | gga | tgt | 528 |
| Thr | Arg | His | Gln | Asn | Glu | Asp | Gly | Ser | Thr | Gln | Asn | Leu | Pro | Gly | Cys | |
| | | | | 160 | | | | | 165 | | | | | 170 | | |
| gtt | gtt | gca | gtg | gcc | aca | tgg | gcc | cat | tgt | ttc | gct | tgt | gaa | tat | taa | 576 |
| Val | Val | Ala | Val | Ala | Thr | Trp | Ala | His | Cys | Phe | Ala | Cys | Glu | Tyr | | |
| | | | 175 | | | | | 180 | | | | | 185 | | | |
| caa | aca | tgc | att | tta | cgt | tgt | tac | cgc | tca | caa | tgt | ata | cat | tgt | aca | 624 |
| Gln | Thr | Cys | Ile | Leu | Arg | Cys | Tyr | Arg | Leu | Gln | Cys | Ile | His | Cys | Thr | |
| | | | 190 | | | | | 195 | | | | | 200 | | | |
| tga | tgg | ctc | gta | tca | tcc | gac | tgg | atc | cat | ggc | cca | gct | cca | aca | ggc | 672 |
| Trp | Leu | Val | Ser | Ser | Asp | Trp | Ile | His | Gly | Pro | Ala | Pro | Thr | Gly | | |
| | | 205 | | | | | 210 | | | | | 215 | | | | |

-continued

```
aga aaa taa tat cac taa ttc caa aaa aga aat gac aaa gct acg aga        720
Arg Lys     Tyr His     Phe Gln Lys Arg Asn Asp Lys Ala Thr Arg
        220                     225                 230 aaa agt gaa aaa ggc cga gaa aga aaa att gga cgc cat taa ccg ggc        768
Lys Ser Glu Lys Gly Arg Glu Arg Lys Ile Gly Arg His     Pro Gly
            235                 240                         245 aac caa gct gga aga gga acg aaa cca agc gta caa agc agc aca caa        816
Asn Gln Ala Gly Arg Gly Thr Lys Pro Ser Val Gln Ser Ser Thr Gln
                250                 255                 260 ggc aga gga gga aaa ggc taa aac att tca acg cct tat aac att tga        864
Gly Arg Gly Gly Lys Gly     Asn Ile Ser Thr Pro Tyr Asn Ile
                265                     270                 275 gtc gga aaa tat taa ctt aaa gaa aag gcc aaa tga cgc agt ttc aaa        912
Val Gly Lys Tyr     Leu Lys Glu Lys Ala Lys     Arg Ser Phe Lys
            280                 285                         290 tcg gga taa gaa aaa aaa ttc tga aac cgc aaa aac tga cga agt aga        960
Ser Gly     Glu Lys Lys Phe     Asn Arg Lys Asn     Arg Ser Arg
                    295                 300 gaa aca gag ggc ggc tga ggc tgc caa ggc cgt gga gac gga gaa gca       1008
Glu Thr Glu Gly Gly     Gly Cys Gln Gly Arg Gly Asp Gly Glu Ala
        305                 310                 315 gag ggc agc tga ggc cac gaa ggt tgc cga agc gga gaa gcg gaa ggc       1056
Glu Gly Ser     Gly His Glu Gly Cys Arg Ser Gly Glu Ala Glu Gly
        320                 325                 330 agc tga ggc cgc caa ggc cgt gga gac gga gaa gca gag ggc agc tga       1104
Ser     Gly Arg Gln Gly Arg Gly Asp Gly Glu Ala Glu Gly Ser
    335                 340                 345 agc cac gaa ggt tgc cga agc gga gaa gca gaa ggc agc tga ggc cgc       1152
Ser His Glu Gly Cys Arg Ser Gly Glu Ala Glu Gly Ser     Gly Arg
        350                 355                 360 caa ggc cgt gga gac gga gaa gca gag ggc agc tga agc cac gaa ggt       1200
Gln Gly Arg Gly Asp Gly Glu Ala Glu Gly Ser     Ser His Glu Gly
    365                 370                     375 tgc cga agc gga gaa gca gag ggc agc tga agc cat gaa ggt tgc cga       1248
Cys Arg Ser Gly Glu Ala Glu Gly Ser     Ser His Glu Gly Cys Arg
        380                 385                     390 agc gga gaa gca gaa ggc agc tga ggc cgc caa ggc cgt gga gac gga       1296
Ser Gly Glu Ala Glu Gly Ser     Gly Arg Gln Gly Arg Gly Asp Gly
    395                 400                 405 gaa gca gag ggc agc tga agc cac gaa ggt tgc cga agc gga gaa gca       1344
Glu Ala Glu Gly Ser     Ser His Glu Gly Cys Arg Ser Gly Glu Ala
        410                 415                 420 gaa ggc agc tga ggc cgc caa ggc cgt gga gac gga gaa gca gag ggc       1392
Glu Gly Ser     Gly Arg Gln Gly Arg Gly Asp Gly Glu Ala Glu Gly
        425                 430                 435 agc tga agc cac gaa ggt tgc cga agc gga gaa gca gaa ggc agc tga       1440
Ser     Ser His Glu Gly Cys Arg Ser Gly Glu Ala Glu Gly Ser
    440                 445                 450 ggc cgc caa ggc cgt gga gac gga gaa gca gag ggc agc tga agc cac       1488
Gly Arg Gln Gly Arg Gly Asp Gly Glu Ala Glu Gly Ser     Ser His
        455                 460                 465 gaa ggt tgc cga agc gga gaa gga tat cga tcc                           1521
Glu Gly Cys Arg Ser Gly Glu Gly Tyr Arg Ser
        470                 475
```

<210> SEQ ID NO 2
<211> LENGTH: 7
<212> TYPE: PRT
<213> ORGANISM: Trypanosoma cruzi

<400> SEQUENCE: 2

```
Tyr Gly Pro Ser Cys Gly Ala
  1               5
```

<210> SEQ ID NO 3
<211> LENGTH: 46
<212> TYPE: PRT
<213> ORGANISM: Trypanosoma cruzi

<400> SEQUENCE: 3

```
Gly Trp Ser Ala Leu Arg Gly Gly Gln Cys Gln Gln Pro Arg Ser Arg
  1               5                  10                  15

Asn Leu Gln Trp Arg Cys His Phe Val Tyr Tyr Gly Arg Thr Ala Gly
              20                  25                  30

Pro Ile Val His Gln Thr Val Gln Pro Tyr Lys Trp Arg Ser
          35                  40                  45
```

<210> SEQ ID NO 4
<211> LENGTH: 36
<212> TYPE: PRT
<213> ORGANISM: Trypanosoma cruzi

<400> SEQUENCE: 4

```
Leu Val Cys Val Gly His Gly Gln Ile Thr His His Phe Cys Pro Thr
  1               5                  10                  15

Ser Glu Lys Asn Val His His Ser Val Tyr Asn Arg Ile Pro Ala Gly
              20                  25                  30

Cys Ser Ser Asn
          35
```

<210> SEQ ID NO 5
<211> LENGTH: 18
<212> TYPE: PRT
<213> ORGANISM: Trypanosoma cruzi

<400> SEQUENCE: 5

```
Arg Glu Glu Ser Phe Asp Val Cys His Leu Gln Phe His Glu Asn Ser
  1               5                  10                  15

Cys Asp
```

<210> SEQ ID NO 6
<211> LENGTH: 32
<212> TYPE: PRT
<213> ORGANISM: Trypanosoma cruzi

<400> SEQUENCE: 6

```
Tyr Ala Gly Ser His Asn Pro Glu Gly Val Leu Ala Ser Trp Lys Cys
  1               5                  10                  15

Gly Leu His Gly Leu Ser Glu Phe Pro His Ala His Asp Arg Gly Gly
              20                  25                  30
```

<210> SEQ ID NO 7
<211> LENGTH: 47
<212> TYPE: PRT
<213> ORGANISM: Trypanosoma cruzi

<400> SEQUENCE: 7

```
Thr Pro Leu Leu Arg His Ile Lys Trp Asn Pro Ile His Val Phe
  1               5                  10                  15

Thr Arg His Gln Asn Glu Asp Gly Ser Thr Gln Asn Leu Pro Gly Cys
              20                  25                  30

Val Val Ala Val Ala Thr Trp Ala His Cys Phe Ala Cys Glu Tyr
```

```
                35                  40                  45
```

<210> SEQ ID NO 8
<211> LENGTH: 16
<212> TYPE: PRT
<213> ORGANISM: Trypanosoma cruzi

<400> SEQUENCE: 8

Gln Thr Cys Ile Leu Arg Cys Tyr Arg Leu Gln Cys Ile His Cys Thr
1               5                   10                  15

<210> SEQ ID NO 9
<211> LENGTH: 17
<212> TYPE: PRT
<213> ORGANISM: Trypanosoma cruzi

<400> SEQUENCE: 9

Trp Leu Val Ser Ser Asp Trp Ile His Gly Pro Ala Pro Thr Gly Arg
1               5                   10                  15

Lys

<210> SEQ ID NO 10
<211> LENGTH: 23
<212> TYPE: PRT
<213> ORGANISM: Trypanosoma cruzi

<400> SEQUENCE: 10

Phe Gln Lys Arg Asn Asp Lys Ala Thr Arg Lys Ser Glu Lys Gly Arg
1               5                   10                  15

Glu Arg Lys Ile Gly Arg His
                20

<210> SEQ ID NO 11
<211> LENGTH: 24
<212> TYPE: PRT
<213> ORGANISM: Trypanosoma cruzi

<400> SEQUENCE: 11

Pro Gly Asn Gln Ala Gly Arg Gly Thr Lys Pro Ser Val Gln Ser Ser
1               5                   10                  15

Thr Gln Gly Arg Gly Gly Lys Gly
                20

<210> SEQ ID NO 12
<211> LENGTH: 8
<212> TYPE: PRT
<213> ORGANISM: Trypanosoma cruzi

<400> SEQUENCE: 12

Asn Ile Ser Thr Pro Tyr Asn Ile
1               5

<210> SEQ ID NO 13
<211> LENGTH: 4
<212> TYPE: PRT
<213> ORGANISM: Trypanosoma cruzi

<400> SEQUENCE: 13

Val Gly Lys Tyr
1

<210> SEQ ID NO 14
<211> LENGTH: 6
<212> TYPE: PRT

```
<213> ORGANISM: Trypanosoma cruzi

<400> SEQUENCE: 14

Leu Lys Glu Lys Ala Lys
 1               5

<210> SEQ ID NO 15
<211> LENGTH: 6
<212> TYPE: PRT
<213> ORGANISM: Trypanosoma cruzi

<400> SEQUENCE: 15

Arg Ser Phe Lys Ser Gly
 1               5

<210> SEQ ID NO 16
<211> LENGTH: 4
<212> TYPE: PRT
<213> ORGANISM: Trypanosoma cruzi

<400> SEQUENCE: 16

Glu Lys Lys Phe
 1

<210> SEQ ID NO 17
<211> LENGTH: 4
<212> TYPE: PRT
<213> ORGANISM: Trypanosoma cruzi

<400> SEQUENCE: 17

Asn Arg Lys Asn
 1

<210> SEQ ID NO 18
<211> LENGTH: 8
<212> TYPE: PRT
<213> ORGANISM: Trypanosoma cruzi

<400> SEQUENCE: 18

Arg Ser Arg Glu Thr Glu Gly Gly
 1               5

<210> SEQ ID NO 19
<211> LENGTH: 13
<212> TYPE: PRT
<213> ORGANISM: Trypanosoma cruzi

<400> SEQUENCE: 19

Gly Cys Gln Gly Arg Gly Asp Gly Glu Ala Glu Gly Ser
 1               5                  10

<210> SEQ ID NO 20
<211> LENGTH: 13
<212> TYPE: PRT
<213> ORGANISM: Trypanosoma cruzi

<400> SEQUENCE: 20

Gly His Glu Gly Cys Arg Ser Gly Glu Ala Glu Gly Ser
 1               5                  10

<210> SEQ ID NO 21
<211> LENGTH: 13
<212> TYPE: PRT
<213> ORGANISM: Trypanosoma cruzi

<400> SEQUENCE: 21
```

Gly Arg Gln Gly Arg Gly Asp Gly Glu Ala Glu Gly Ser
1               5                   10

<210> SEQ ID NO 22
<211> LENGTH: 13
<212> TYPE: PRT
<213> ORGANISM: Trypanosoma cruzi

<400> SEQUENCE: 22

Ser His Glu Gly Cys Arg Ser Gly Glu Ala Glu Gly Ser
1               5                   10

<210> SEQ ID NO 23
<211> LENGTH: 13
<212> TYPE: PRT
<213> ORGANISM: Trypanosoma cruzi

<400> SEQUENCE: 23

Gly Arg Gln Gly Arg Gly Asp Gly Glu Ala Glu Gly Ser
1               5                   10

<210> SEQ ID NO 24
<211> LENGTH: 13
<212> TYPE: PRT
<213> ORGANISM: Trypanosoma cruzi

<400> SEQUENCE: 24

Ser His Glu Gly Cys Arg Ser Gly Glu Ala Glu Gly Ser
1               5                   10

<210> SEQ ID NO 25
<211> LENGTH: 13
<212> TYPE: PRT
<213> ORGANISM: Trypanosoma cruzi

<400> SEQUENCE: 25

Ser His Glu Gly Cys Arg Ser Gly Glu Ala Glu Gly Ser
1               5                   10

<210> SEQ ID NO 26
<211> LENGTH: 13
<212> TYPE: PRT
<213> ORGANISM: Trypanosoma cruzi

<400> SEQUENCE: 26

Gly Arg Gln Gly Arg Gly Asp Gly Glu Ala Glu Gly Ser
1               5                   10

<210> SEQ ID NO 27
<211> LENGTH: 13
<212> TYPE: PRT
<213> ORGANISM: Trypanosoma cruzi

<400> SEQUENCE: 27

Ser His Glu Gly Cys Arg Ser Gly Glu Ala Glu Gly Ser
1               5                   10

<210> SEQ ID NO 28
<211> LENGTH: 13
<212> TYPE: PRT
<213> ORGANISM: Trypanosoma cruzi

<400> SEQUENCE: 28

Gly Arg Gln Gly Arg Gly Asp Gly Glu Ala Glu Gly Ser
1               5                   10

<210> SEQ ID NO 29
<211> LENGTH: 13
<212> TYPE: PRT
<213> ORGANISM: Trypanosoma cruzi

<400> SEQUENCE: 29

Ser His Glu Gly Cys Arg Ser Gly Glu Ala Glu Gly Ser
 1               5                  10

<210> SEQ ID NO 30
<211> LENGTH: 13
<212> TYPE: PRT
<213> ORGANISM: Trypanosoma cruzi

<400> SEQUENCE: 30

Gly Arg Gln Gly Arg Gly Asp Gly Glu Ala Glu Gly Ser
 1               5                  10

<210> SEQ ID NO 31
<211> LENGTH: 13
<212> TYPE: PRT
<213> ORGANISM: Trypanosoma cruzi

<400> SEQUENCE: 31

Ser His Glu Gly Cys Arg Ser Gly Glu Gly Tyr Arg Ser
 1               5                  10

<210> SEQ ID NO 32
<211> LENGTH: 42
<212> TYPE: DNA
<213> ORGANISM: Trypanosoma cruzi
<220> FEATURE:
<221> NAME/KEY: modified_base
<222> LOCATION: (1)..(4)
<223> OTHER INFORMATION: a, t, c, g

<400> SEQUENCE: 32
nnnnctatta ttgatacagt tctgtacta tattggttgt gc                     42

<210> SEQ ID NO 33
<211> LENGTH: 3749
<212> TYPE: DNA
<213> ORGANISM: Trypanosoma cruzi
<220> FEATURE:
<221> NAME/KEY: CDS
<222> LOCATION: (833)..(2575)
<220> FEATURE:
<221> NAME/KEY: sig_peptide
<222> LOCATION: (822)..(937)
<220> FEATURE:
<221> NAME/KEY: mat_peptide
<222> LOCATION: (938)..(2575)

<400> SEQUENCE: 33 cccctcgag gtcgacctgc aggtcaacgg atcttacctg agtacaaaag gtcaagtgag      60
cggtcaaaag gatgtatata tacatatata accataaggg aaacatttgg gcatttaact   120
gcctttacat ttccctttc cttcaatatc ttgtttgttt gttttggtt tctataggaa     180 attttaggat ccggccagcg gcataggaga ttattctctt ttttattaat tgcttaatgc   240
gttggtctgt gtgtgtgttg gttcccttgt gcgagctcac ggggcctaat tatgattgtt   300
gcgcatatgc atatatatat atatatatat acatgtgtgt gtgtgtgtat atgtacgttt   360
gttggtttgc cgctgtactc ccgcctgcgt gtgtctgtct ctctctctgt gtgtgtgatg   420
ggctgcttct cttctttttg ttgcgtccct ttattattat tattttttt tcttctctcc    480

| | |
|---|---|
| cacttctctc cccgtgtggt gcacgcacag taaagataga gggagaaata gagcgagtgt | 540 |
| ttgtatcagt gtctccgttg cggctggtac tggtagaagg agaagaatag aagaaggaga | 600 |
| aaaaaaaaaa aaaaaaaaaa aaagagagag gagagagaga agggcgaacg agaaaaaaga | 660 |
| agaagaaaca tttgagaagg aattggaacg aaaattgtaa gaggaagcaa aaaaaaaaaa | 720 |
| aaaaagtgtg tgtgtgtgag agagagagag agaggaagcc aataataata aaagcaaac | 780 |
| aaaaaagcaa aacaaaaat atttgtagac cggacgtccc gtcttggacg tg atg ttt | 838 |

```
                                                           Met Phe
                                                           -35
tca aaa agg acg tcg cca gca ccc ttc cgt gcg ctc ctg ctg ccg gtc       886
Ser Lys Arg Thr Ser Pro Ala Pro Phe Arg Ala Leu Leu Leu Pro Val
        -30                 -25                 -20 gtg gtg gtg gtg gtg gtg gtg gtg gca tct gtg gcc ctc cct gca gga       934
Val Val Val Val Val Val Val Val Ala Ser Val Ala Leu Pro Ala Gly
            -15                 -10                 -5 gcg cag ttt gat tta agg cag cag cag ctg gtt ata cag gat ttc ttc       982
Ala Gln Phe Asp Leu Arg Gln Gln Gln Leu Val Ile Gln Asp Phe Phe
 -1  1               5                  10                  15 atc agt cgc tcc tgc gca gga tgt tca cag ggg caa acc gat ggc cca      1030
Ile Ser Arg Ser Cys Ala Gly Cys Ser Gln Gly Gln Thr Asp Gly Pro
                20                  25                  30 agc ggt gcc ggc aca ctc ttc act gcc gcc ggt ggt tcg ctt ggc aaa      1078
Ser Gly Ala Gly Thr Leu Phe Thr Ala Ala Gly Gly Ser Leu Gly Lys
            35                  40                  45 gat gct tcc acg ctg ctg ttg tgt gac caa ggt ggt ggt ggc tcc agc      1126
Asp Ala Ser Thr Leu Leu Leu Cys Asp Gln Gly Gly Gly Gly Ser Ser
        50                  55                  60 gtg cgt ttg gtg aac aaa tcc ggc att ttc acc ctt gcc ggt agt aaa      1174
Val Arg Leu Val Asn Lys Ser Gly Ile Phe Thr Leu Ala Gly Ser Lys
 65                  70                  75 acg acg cgt ggc aat caa aat ggt ccg gcg gcg acg gca ctc ttc aac      1222
Thr Thr Arg Gly Asn Gln Asn Gly Pro Ala Ala Thr Ala Leu Phe Asn
             80                  85                  90                  95 atg ccc cga gct gtg gtg ctt gag gat gga gcg ctt tac gtg gcg gac      1270
Met Pro Arg Ala Val Val Leu Glu Asp Gly Ala Leu Tyr Val Ala Asp
                100                 105                 110 agt gcc aac aac ctc gtt cga gaa atc tcc aat ggc att gtc act tcg      1318
Ser Ala Asn Asn Leu Val Arg Glu Ile Ser Asn Gly Ile Val Thr Ser
            115                 120                 125 ttt att acg gag gga ctg ctg ggc cca tcg tac atc aaa ccg tac agc      1366
Phe Ile Thr Glu Gly Leu Leu Gly Pro Ser Tyr Ile Lys Pro Tyr Ser
        130                 135                 140 cgt cca aat ggc gcc cat gac ttg ttt gtg tcg gac acg ggc aaa tct      1414
Arg Pro Asn Gly Ala His Asp Leu Phe Val Ser Asp Thr Gly Lys Ser
    145                 150                 155 cgc atc att ttt gcc cca ctt cag aaa caa acg ttc atc aca gtg ttt      1462
Arg Ile Ile Phe Ala Pro Leu Gln Lys Gln Thr Phe Ile Thr Val Phe
160                 165                 170                 175 ata aca gga ttc cag ccg gat gtt ctt caa att agc gag aag agt cgt      1510
Ile Thr Gly Phe Gln Pro Asp Val Leu Gln Ile Ser Glu Lys Ser Arg
                180                 185                 190 ttg atg ttt gcc atc tgc aat tcc acg aaa att ctt tcg att aat atg      1558
Leu Met Phe Ala Ile Cys Asn Ser Thr Lys Ile Leu Ser Ile Asn Met
            195                 200                 205 cag gga gcc aca acc ccg aag gat tac tgg caa gtt gga aat gcg gac      1606
Gln Gly Ala Thr Thr Pro Lys Asp Tyr Trp Gln Val Gly Asn Ala Asp
        210                 215                 220 tgc atg ggc tat cag agt tct ctc atg ctc acg acc gag gag gat aaa      1654
Cys Met Gly Tyr Gln Ser Ser Leu Met Leu Thr Thr Glu Glu Asp Lys
```

|  |  |  |  |  |  |  |  |  |  |  |  |  |  |  |  |
|---|---|---|---|---|---|---|---|---|---|---|---|---|---|---|---|
| Cys | Met | Gly | Tyr | Gln | Ser | Ser | Leu | Met | Leu | Thr | Thr | Glu | Glu | Asp | Lys |
|  | 225 |  |  |  | 230 |  |  |  | 235 |  |  |  |  |  |  |

| ctc | ctc | tac | tac | ggc | ata | tta | aat | gga | acc | cca | tcc | atc | atg | tct | tta | 1702 |
|---|---|---|---|---|---|---|---|---|---|---|---|---|---|---|---|---|
| Leu | Leu | Tyr | Tyr | Gly | Ile | Leu | Asn | Gly | Thr | Pro | Ser | Ile | Met | Ser | Leu |  |
| 240 |  |  |  |  | 245 |  |  |  |  | 250 |  |  |  |  | 255 |  |

| ccc | gcc | acc | aaa | acg | aag | acg | gaa | gca | ccc | aga | att | tgc | ccg | gat | gtg | 1750 |
|---|---|---|---|---|---|---|---|---|---|---|---|---|---|---|---|---|
| Pro | Ala | Thr | Lys | Thr | Lys | Thr | Glu | Ala | Pro | Arg | Ile | Cys | Pro | Asp | Val |  |
|  |  |  |  |  | 260 |  |  |  |  | 265 |  |  |  |  | 270 |  |

| ttg | ttg | cgg | tgg | cca | cat | ggg | ccc | att | gtt | tcg | ctt | gtg | aat | att | aac | 1798 |
|---|---|---|---|---|---|---|---|---|---|---|---|---|---|---|---|---|
| Leu | Leu | Arg | Trp | Pro | His | Gly | Pro | Ile | Val | Ser | Leu | Val | Asn | Ile | Asn |  |
|  |  |  | 275 |  |  |  |  | 280 |  |  |  |  | 285 |  |  |  |

| aaa | cat | gca | ttt | tac | gtt | gtt | acc | gcc | tcc | aat | gta | tac | att | gta | cat | 1846 |
|---|---|---|---|---|---|---|---|---|---|---|---|---|---|---|---|---|
| Lys | His | Ala | Phe | Tyr | Val | Val | Thr | Ala | Ser | Asn | Val | Tyr | Ile | Val | His |  |
|  |  | 290 |  |  |  |  | 295 |  |  |  |  | 300 |  |  |  |  |

| gat | ggc | tct | tat | cat | ccg | act | gtg | acg | ccg | aca | cct | cct | ctg | aca | ccg | 1894 |
|---|---|---|---|---|---|---|---|---|---|---|---|---|---|---|---|---|
| Asp | Gly | Ser | Tyr | His | Pro | Thr | Val | Thr | Pro | Thr | Pro | Pro | Leu | Thr | Pro |  |
|  | 305 |  |  |  |  | 310 |  |  |  |  | 315 |  |  |  |  |  |

| acg | cct | aca | cca | gaa | gtg | aca | ccc | aca | cct | act | gtg | acc | ccg | acg | cct | 1942 |
|---|---|---|---|---|---|---|---|---|---|---|---|---|---|---|---|---|
| Thr | Pro | Thr | Pro | Glu | Val | Thr | Pro | Thr | Pro | Thr | Val | Thr | Pro | Thr | Pro |  |
| 320 |  |  |  |  | 325 |  |  |  |  | 330 |  |  |  |  | 335 |  |

| aca | ccg | gaa | gtg | aca | ccg | aca | ccg | cca | gtg | act | ccg | agc | ccc | acc | atc | 1990 |
|---|---|---|---|---|---|---|---|---|---|---|---|---|---|---|---|---|
| Thr | Pro | Glu | Val | Thr | Pro | Thr | Pro | Pro | Val | Thr | Pro | Ser | Pro | Thr | Ile |  |
|  |  |  |  | 340 |  |  |  |  | 345 |  |  |  |  | 350 |  |  |

| aca | atc | cac | cgg | ggt | ttt | gct | gtg | gca | gcc | ttt | cct | gcc | caa | agt | ctt | 2038 |
|---|---|---|---|---|---|---|---|---|---|---|---|---|---|---|---|---|
| Thr | Ile | His | Arg | Gly | Phe | Ala | Val | Ala | Ala | Phe | Pro | Ala | Gln | Ser | Leu |  |
|  |  |  | 355 |  |  |  |  | 360 |  |  |  |  | 365 |  |  |  |

| cca | atc | gaa | gac | ccg | cgg | ctt | atg | cat | gaa | ctg | ctt | tct | tgg | tta | atg | 2086 |
|---|---|---|---|---|---|---|---|---|---|---|---|---|---|---|---|---|
| Pro | Ile | Glu | Asp | Pro | Arg | Leu | Met | His | Glu | Leu | Leu | Ser | Trp | Leu | Met |  |
|  |  | 370 |  |  |  |  | 375 |  |  |  |  | 380 |  |  |  |  |

| aag | gat | gta | ggg | att | gcg | ttc | gaa | tcc | acg | gac | ttt | ttt | gcc | gta | ttt | 2134 |
|---|---|---|---|---|---|---|---|---|---|---|---|---|---|---|---|---|
| Lys | Asp | Val | Gly | Ile | Ala | Phe | Glu | Ser | Thr | Asp | Phe | Phe | Ala | Val | Phe |  |
| 385 |  |  |  |  | 390 |  |  |  |  | 395 |  |  |  |  |  |  |

| cct | cca | gat | aga | gag | gtt | ttg | gtg | ccc | ggt | tat | gta | aat | gtc | tcc | acc | 2182 |
|---|---|---|---|---|---|---|---|---|---|---|---|---|---|---|---|---|
| Pro | Pro | Asp | Arg | Glu | Val | Leu | Val | Pro | Gly | Tyr | Val | Asn | Val | Ser | Thr |  |
| 400 |  |  |  | 405 |  |  |  |  | 410 |  |  |  |  | 415 |  |  |

| tgg | aat | aac | ttg | acg | gtg | cta | ttc | aac | ttt | gac | cgc | acc | att | gtc | atc | 2230 |
|---|---|---|---|---|---|---|---|---|---|---|---|---|---|---|---|---|
| Trp | Asn | Asn | Leu | Thr | Val | Leu | Phe | Asn | Phe | Asp | Arg | Thr | Ile | Val | Ile |  |
|  |  |  | 420 |  |  |  |  | 425 |  |  |  |  | 430 |  |  |  |

| acg | gaa | tat | ttc | act | cca | gag | ggc | atg | tct | tca | gag | gag | gga | cag | gcc | 2278 |
|---|---|---|---|---|---|---|---|---|---|---|---|---|---|---|---|---|
| Thr | Glu | Tyr | Phe | Thr | Pro | Glu | Gly | Met | Ser | Ser | Glu | Glu | Gly | Gln | Ala |  |
|  |  |  | 435 |  |  |  |  | 440 |  |  |  |  | 445 |  |  |  |

| cga | ctc | ttc | gct | tcg | ccg | tgg | tac | tgg | acg | aga | aat | ttc | ctt | gat | tca | 2326 |
|---|---|---|---|---|---|---|---|---|---|---|---|---|---|---|---|---|
| Arg | Leu | Phe | Ala | Ser | Pro | Trp | Tyr | Trp | Thr | Arg | Asn | Phe | Leu | Asp | Ser |  |
|  |  | 450 |  |  |  |  | 455 |  |  |  |  | 460 |  |  |  |  |

| tta | aag | aaa | aca | gta | gct | tgg | aag | gac | ttg | gag | gcg | ttt | tgc | atg | gtc | 2374 |
|---|---|---|---|---|---|---|---|---|---|---|---|---|---|---|---|---|
| Leu | Lys | Lys | Thr | Val | Ala | Trp | Lys | Asp | Leu | Glu | Ala | Phe | Cys | Met | Val |  |
| 465 |  |  |  |  | 470 |  |  |  |  | 475 |  |  |  |  |  |  |

| aac | tgt | gtt | gaa | cac | tgt | gag | aca | atg | aca | ttc | cat | aag | tca | gaa | tgt | 2422 |
|---|---|---|---|---|---|---|---|---|---|---|---|---|---|---|---|---|
| Asn | Cys | Val | Glu | His | Cys | Glu | Thr | Met | Thr | Phe | His | Lys | Ser | Glu | Cys |  |
| 480 |  |  |  |  | 485 |  |  |  |  | 490 |  |  |  |  | 495 |  |

| gta | ggc | tac | gtc | cgg | ccc | cca | gta | tgc | aac | gac | gtc | tgt | gtg | ggg | gcg | 2470 |
|---|---|---|---|---|---|---|---|---|---|---|---|---|---|---|---|---|
| Val | Gly | Tyr | Val | Arg | Pro | Pro | Val | Cys | Asn | Asp | Val | Cys | Val | Gly | Ala |  |
|  |  |  |  | 500 |  |  |  |  | 505 |  |  |  |  | 510 |  |  |

| gta | gtg | tcc | tcc | gtg | gtg | ctt | ggc | gcc | aca | ggt | atc | gca | ctc | att | gca | 2518 |
|---|---|---|---|---|---|---|---|---|---|---|---|---|---|---|---|---|
| Val | Val | Ser | Ser | Val | Val | Leu | Gly | Ala | Thr | Gly | Ile | Ala | Leu | Ile | Ala |  |
|  |  |  | 515 |  |  |  |  | 520 |  |  |  |  | 525 |  |  |  |

| ctg | atg | gtt | gga | agt | tcg | gcg | aac | tta | cgg | agc | gct | gtg | att | ctt | gtt | 2566 |
|---|---|---|---|---|---|---|---|---|---|---|---|---|---|---|---|---|
| Leu | Met | Val | Gly | Ser | Ser | Ala | Asn | Leu | Arg | Ser | Ala | Val | Ile | Leu | Val |  |
|  |  |  |  | 530 |  |  |  |  | 535 |  |  |  |  | 540 |  |  |

| cca | ccc | atg | tagattttgt | ccccacactt | tggagaaagg | tgggaaatga |  | 2615 |
|---|---|---|---|---|---|---|---|---|

```
Pro Pro Met
    545 cttcagaaat tgaaattaga aggaaccaac aacacaagaa gcaagcgaag gtgaaaacaa    2675 cgggaagaag aagaagaaga aaaaaaaaaa aagaaaagaa aaaatggggg ggctgagtgg    2735 ggaaaagaga aagaaaagaa gtgtgcgtgt aaccgtgtgt gtgtgtgccg gggaaaaaga    2795 agaaacacaa aagatttctt ttttgttttt tgttttaatg gtgcaaagag ggaaacaaga    2855 aagcgaaggg tgcatgtgtg tctgtagata tataaaaata aacatatgcc cccgcatgta    2915 tttaccgtt ggcagttccg tggcttcttt tttttttttt tttttgtatt tttgttattt     2975 tttcctctta tttcttcgtg tgtgtgtgta tgtattatta ttcttttttg tttttttgttt   3035 gtttgtttgt ttttacctac tcatctgcct tcatttttt tttttgtgtgt tttcactcag    3095 ccctctctc tttctctctt cttcttctct cttcatgcgt gtatttccgc atggagtgga    3155 aaaggaacgg ctgggagcga ttgtgatggt gcttgtgttg gaggtgtggc tatgcgagta    3215 gtggagatgc atgtatgtat gtatatatgt ggtttggtgt atatatttaa atattatatg    3275 ttgttgttgt tgctgtccga ctctcggggg acgtacaccg acctacttac ttacagagag    3335 agagagagag aggaagagaa tgagagaaaa ggggggcgtg tggtgtgttc tgtattcatt    3395 gaagagcgca aaataaaata aaaataaaat aataaaatga gggagagaga agggaggagg    3455 aaacagcaga ggaatttgta tgccatcgtt gtgactaatt tttcataagg actctgtgat    3515 ggccctgtta accacgtcca ctgcagtaga cgagtcaaaa ttgactgcga gtgttacgcc    3575 aactgtacgt ctgtctccct cgtgctgtac gtgtgcaagt aagtacgtgt gtgcactgtg    3635 cgtgtgcgtg tgtgtgtgtg tcaagggcgc cttttacgtg tctgtgcgct tgagtgggga    3695 ggggagaaga ggaggagaga cgaagaaaga aagaaagaaa aaagcgggcg gcgc          3749

<210> SEQ ID NO 34
<211> LENGTH: 581
<212> TYPE: PRT
<213> ORGANISM: Trypanosoma cruzi

<400> SEQUENCE: 34

Met Phe Ser Lys Arg Thr Ser Pro Ala Pro Phe Arg Ala Leu Leu Leu
-35                 -30                 -25                 -20

Pro Val Val Val Val Val Val Val Val Ala Ser Val Ala Leu Pro
            -15                 -10                  -5

Ala Gly Ala Gln Phe Asp Leu Arg Gln Gln Gln Leu Val Ile Gln Asp
        -1   1               5                  10

Phe Phe Ile Ser Arg Ser Cys Ala Gly Cys Ser Gln Gly Gln Thr Asp
        15                  20                  25

Gly Pro Ser Gly Ala Gly Thr Leu Phe Thr Ala Gly Gly Ser Leu
    30                  35                  40                  45

Gly Lys Asp Ala Ser Thr Leu Leu Leu Cys Asp Gln Gly Gly Gly Gly
                50                  55                  60

Ser Ser Val Arg Leu Val Asn Lys Ser Gly Ile Phe Thr Leu Ala Gly
                65                  70                  75

Ser Lys Thr Thr Arg Gly Asn Gln Asn Gly Pro Ala Ala Thr Ala Leu
            80                  85                  90

Phe Asn Met Pro Arg Ala Val Val Leu Glu Asp Gly Ala Leu Tyr Val
        95                  100                 105

Ala Asp Ser Ala Asn Asn Leu Val Arg Glu Ile Ser Asn Gly Ile Val
110                 115                 120                 125

Thr Ser Phe Ile Thr Glu Gly Leu Leu Gly Pro Ser Tyr Ile Lys Pro
```

```
                       130                 135                 140
Tyr Ser Arg Pro Asn Gly Ala His Asp Leu Phe Val Ser Asp Thr Gly
            145                 150                 155
Lys Ser Arg Ile Ile Phe Ala Pro Leu Gln Lys Gln Thr Phe Ile Thr
            160                 165                 170
Val Phe Ile Thr Gly Phe Gln Pro Asp Val Leu Gln Ile Ser Glu Lys
175                 180                 185
Ser Arg Leu Met Phe Ala Ile Cys Asn Ser Thr Lys Ile Leu Ser Ile
190                 195                 200                 205
Asn Met Gln Gly Ala Thr Thr Pro Lys Asp Tyr Trp Gln Val Gly Asn
                    210                 215                 220
Ala Asp Cys Met Gly Tyr Gln Ser Ser Leu Met Leu Thr Thr Glu Glu
                    225                 230                 235
Asp Lys Leu Leu Tyr Tyr Gly Ile Leu Asn Gly Thr Pro Ser Ile Met
            240                 245                 250
Ser Leu Pro Ala Thr Lys Thr Lys Thr Glu Ala Pro Arg Ile Cys Pro
            255                 260                 265
Asp Val Leu Leu Arg Trp Pro His Gly Pro Ile Val Ser Leu Val Asn
270                 275                 280                 285
Ile Asn Lys His Ala Phe Tyr Val Val Thr Ala Ser Asn Val Tyr Ile
                    290                 295                 300
Val His Asp Gly Ser Tyr His Pro Thr Val Thr Pro Thr Pro Pro Leu
                    305                 310                 315
Thr Pro Thr Pro Thr Pro Glu Val Thr Pro Thr Pro Thr Val Thr Pro
            320                 325                 330
Thr Pro Thr Pro Glu Val Thr Pro Thr Pro Pro Val Thr Pro Ser Pro
            335                 340                 345
Thr Ile Thr Ile His Arg Gly Phe Ala Val Ala Ala Phe Pro Ala Gln
350                 355                 360                 365
Ser Leu Pro Ile Glu Asp Pro Arg Leu Met His Glu Leu Leu Ser Trp
                    370                 375                 380
Leu Met Lys Asp Val Gly Ile Ala Phe Glu Ser Thr Asp Phe Phe Ala
                    385                 390                 395
Val Phe Pro Pro Asp Arg Glu Val Leu Val Pro Gly Tyr Val Asn Val
            400                 405                 410
Ser Thr Trp Asn Asn Leu Thr Val Leu Phe Asn Phe Asp Arg Thr Ile
            415                 420                 425
Val Ile Thr Glu Tyr Phe Thr Pro Glu Gly Met Ser Ser Glu Glu Gly
430                 435                 440                 445
Gln Ala Arg Leu Phe Ala Ser Pro Trp Tyr Trp Thr Arg Asn Phe Leu
                    450                 455                 460
Asp Ser Leu Lys Lys Thr Val Ala Trp Lys Asp Leu Glu Ala Phe Cys
                    465                 470                 475
Met Val Asn Cys Val Glu His Cys Glu Thr Met Thr Phe His Lys Ser
            480                 485                 490
Glu Cys Val Gly Tyr Val Arg Pro Pro Val Cys Asn Asp Val Cys Val
    495                 500                 505
Gly Ala Val Val Ser Val Val Leu Gly Ala Thr Gly Ile Ala Leu
510                 515                 520                 525
Ile Ala Leu Met Val Gly Ser Ser Ala Asn Leu Arg Ser Ala Val Ile
                    530                 535                 540
Leu Val Pro Pro Met
            545
```

-continued

```
<210> SEQ ID NO 35
<211> LENGTH: 2151
<212> TYPE: DNA
<213> ORGANISM: Trypanosoma cruzi
<220> FEATURE:
<221> NAME/KEY: CDS
<222> LOCATION: (1)..(2151)

<400> SEQUENCE: 35
```

| | | | | | | | | | | | | | | | | |
|---|---|---|---|---|---|---|---|---|---|---|---|---|---|---|---|---|
| atg | gcc | cga | gct | gtg | gtg | ctt | gag | gat | gga | gcg | ctt | tac | gtg | gcg | gac | 48 |
| Met | Ala | Arg | Ala | Val | Val | Leu | Glu | Asp | Gly | Ala | Leu | Tyr | Val | Ala | Asp | |
| 1 | | | | 5 | | | | | 10 | | | | | 15 | | |
| aat | gcc | aac | aac | ctc | gtt | cga | gaa | atc | tcc | aat | ggc | gtt | gtc | act | tcg | 96 |
| Asn | Ala | Asn | Asn | Leu | Val | Arg | Glu | Ile | Ser | Asn | Gly | Val | Val | Thr | Ser | |
| | | | 20 | | | | | 25 | | | | | 30 | | | |
| ttt | att | acg | gaa | gga | ctg | ctg | ggc | cca | tcg | tac | atc | aaa | ccg | tac | agc | 144 |
| Phe | Ile | Thr | Glu | Gly | Leu | Leu | Gly | Pro | Ser | Tyr | Ile | Lys | Pro | Tyr | Ser | |
| | | 35 | | | | | 40 | | | | | 45 | | | | |
| cgt | aca | aat | ggc | gct | cat | gac | ttg | ttt | gtg | tcg | gac | acg | ggc | aaa | tca | 192 |
| Arg | Thr | Asn | Gly | Ala | His | Asp | Leu | Phe | Val | Ser | Asp | Thr | Gly | Lys | Ser | |
| | 50 | | | | | 55 | | | | | 60 | | | | | |
| cgc | atc | att | ttt | gcc | cca | cct | cag | aaa | aaa | acg | ttc | atc | aca | gtg | ttt | 240 |
| Arg | Ile | Ile | Phe | Ala | Pro | Pro | Gln | Lys | Lys | Thr | Phe | Ile | Thr | Val | Phe | |
| 65 | | | | | 70 | | | | | 75 | | | | | 80 | |
| ata | aca | gga | ttc | cag | ccg | gat | gtt | ctt | caa | att | agc | gag | aag | agt | cgt | 288 |
| Ile | Thr | Gly | Phe | Gln | Pro | Asp | Val | Leu | Gln | Ile | Ser | Glu | Lys | Ser | Arg | |
| | | | | 85 | | | | | 90 | | | | | 95 | | |
| ttg | atg | ttt | gcc | atc | tgc | aat | tcc | acg | aaa | att | ctt | gcg | att | aat | atg | 336 |
| Leu | Met | Phe | Ala | Ile | Cys | Asn | Ser | Thr | Lys | Ile | Leu | Ala | Ile | Asn | Met | |
| | | | 100 | | | | | 105 | | | | | 110 | | | |
| cag | gga | gcc | aca | acc | ccg | aag | gag | tac | tgg | caa | gtt | gga | aat | gcg | gac | 384 |
| Gln | Gly | Ala | Thr | Thr | Pro | Lys | Glu | Tyr | Trp | Gln | Val | Gly | Asn | Ala | Asp | |
| | | | 115 | | | | | 120 | | | | | 125 | | | |
| tgc | atg | ggc | tat | cag | agt | tcc | ctc | atg | ctc | acg | acc | gag | gag | gat | aaa | 432 |
| Cys | Met | Gly | Tyr | Gln | Ser | Ser | Leu | Met | Leu | Thr | Thr | Glu | Glu | Asp | Lys | |
| | | 130 | | | | | 135 | | | | | 140 | | | | |
| ctc | ctc | tac | tac | ggc | ata | tta | aat | gga | acc | cca | tcc | atc | atg | tct | tta | 480 |
| Leu | Leu | Tyr | Tyr | Gly | Ile | Leu | Asn | Gly | Thr | Pro | Ser | Ile | Met | Ser | Leu | |
| 145 | | | | | 150 | | | | | 155 | | | | | 160 | |
| ccc | gcc | acc | aaa | acg | aag | acg | gaa | gca | ccc | aga | att | tgc | ccg | gat | gtg | 528 |
| Pro | Ala | Thr | Lys | Thr | Lys | Thr | Glu | Ala | Pro | Arg | Ile | Cys | Pro | Asp | Val | |
| | | | | 165 | | | | | 170 | | | | | 175 | | |
| ttg | ttg | cag | tgg | cca | cat | ggg | ccc | att | gtt | tcg | ctt | gtg | aat | att | aac | 576 |
| Leu | Leu | Gln | Trp | Pro | His | Gly | Pro | Ile | Val | Ser | Leu | Val | Asn | Ile | Asn | |
| | | | 180 | | | | | 185 | | | | | 190 | | | |
| aaa | cat | gca | ttt | tac | gtt | gtt | acc | gcc | tcc | aat | gta | tac | att | gta | cat | 624 |
| Lys | His | Ala | Phe | Tyr | Val | Val | Thr | Ala | Ser | Asn | Val | Tyr | Ile | Val | His | |
| | | | 195 | | | | | 200 | | | | | 205 | | | |
| gat | ggc | tcg | tat | cat | ccg | act | gga | tcc | atg | gcc | cag | ctc | caa | cag | gca | 672 |
| Asp | Gly | Ser | Tyr | His | Pro | Thr | Gly | Ser | Met | Ala | Gln | Leu | Gln | Gln | Ala | |
| | | 210 | | | | | 215 | | | | | 220 | | | | |
| gaa | aat | aat | atc | act | aat | tcc | aaa | aaa | gaa | atg | aca | aag | cta | cga | gaa | 720 |
| Glu | Asn | Asn | Ile | Thr | Asn | Ser | Lys | Lys | Glu | Met | Thr | Lys | Leu | Arg | Glu | |
| 225 | | | | | 230 | | | | | 235 | | | | | 240 | |
| aaa | gtg | aaa | aag | gcc | gag | aaa | gaa | aaa | ttg | gac | gcc | att | aac | cgg | gca | 768 |
| Lys | Val | Lys | Lys | Ala | Glu | Lys | Glu | Lys | Leu | Asp | Ala | Ile | Asn | Arg | Ala | |
| | | | | 245 | | | | | 250 | | | | | 255 | | |
| acc | aag | ctg | gaa | gag | gaa | cga | aac | caa | gcg | tac | aaa | gca | gca | cac | aag | 816 |
| Thr | Lys | Leu | Glu | Glu | Glu | Arg | Asn | Gln | Ala | Tyr | Lys | Ala | Ala | His | Lys | |
| | | | 260 | | | | | 265 | | | | | 270 | | | |
| gca | gag | gag | gaa | aag | gct | aaa | aca | ttt | caa | cgc | ctt | ata | aca | ttt | gag | 864 |

-continued

| | | |
|---|---|---|
| Ala Glu Glu Glu Lys Ala Lys Thr Phe Gln Arg Leu Ile Thr Phe Glu<br>     275                   280                   285 | | |
| tcg gaa aat att aac tta aag aaa agg cca aat gac gca gtt tca aat<br>Ser Glu Asn Ile Asn Leu Lys Lys Arg Pro Asn Asp Ala Val Ser Asn<br>290                   295                   300 | 912 | |
| cgg gat aag aaa aaa aat tct gaa acc gca aaa act gac gaa gta gag<br>Arg Asp Lys Lys Lys Asn Ser Glu Thr Ala Lys Thr Asp Glu Val Glu<br>305                   310                   315                   320 | 960 | |
| aaa cag agg gcg gct gag gct gcc aag gcc gtg gag acg gag aag cag<br>Lys Gln Arg Ala Ala Glu Ala Ala Lys Ala Val Glu Thr Glu Lys Gln<br>                   325                   330                   335 | 1008 | |
| agg gca gct gag gcc acg aag gtt gcc gaa gcg gag aag cgg aag gca<br>Arg Ala Ala Glu Ala Thr Lys Val Ala Glu Ala Glu Lys Arg Lys Ala<br>              340                   345                   350 | 1056 | |
| gct gag gcc gcc aag gcc gtg gag acg gag aag cag agg gca gct gaa<br>Ala Glu Ala Ala Lys Ala Val Glu Thr Glu Lys Gln Arg Ala Ala Glu<br>                   355                   360                   365 | 1104 | |
| gcc acg aag gtt gcc gaa gcg gag aag cag aag gca gct gag gcc gcc<br>Ala Thr Lys Val Ala Glu Ala Glu Lys Gln Lys Ala Ala Glu Ala Ala<br>370                   375                   380 | 1152 | |
| aag gcc gtg gag acg gag aag cag agg gca gct gaa gcc acg aag gtt<br>Lys Ala Val Glu Thr Glu Lys Gln Arg Ala Ala Glu Ala Thr Lys Val<br>385                   390                   395                   400 | 1200 | |
| gcc gaa gcg gag aag cag agg gca gct gaa gcc atg aag gtt gcc gaa<br>Ala Glu Ala Glu Lys Gln Arg Ala Ala Glu Ala Met Lys Val Ala Glu<br>                   405                   410                   415 | 1248 | |
| gcg gag aag cag aag gca gct gag gcc gcc aag gcc gtg gag acg gag<br>Ala Glu Lys Gln Lys Ala Ala Glu Ala Ala Lys Ala Val Glu Thr Glu<br>              420                   425                   430 | 1296 | |
| aag cag agg gca gct gaa gcc acg aag gtt gcc gaa gcg gag aag cag<br>Lys Gln Arg Ala Ala Glu Ala Thr Lys Val Ala Glu Ala Glu Lys Gln<br>                   435                   440                   445 | 1344 | |
| aag gca gct gag gcc gcc aag gcc gtg gag acg gag aag cag agg gca<br>Lys Ala Ala Glu Ala Ala Lys Ala Val Glu Thr Glu Lys Gln Arg Ala<br>450                   455                   460 | 1392 | |
| gct gaa gcc acg aag gtt gcc gaa gcg gag aag cag aag gca gct gag<br>Ala Glu Ala Thr Lys Val Ala Glu Ala Glu Lys Gln Lys Ala Ala Glu<br>465                   470                   475                   480 | 1440 | |
| gcc gcc aag gcc gtg gag acg gag aag cag agg gca gct gaa gcc acg<br>Ala Ala Lys Ala Val Glu Thr Glu Lys Gln Arg Ala Ala Glu Ala Thr<br>                   485                   490                   495 | 1488 | |
| aag gtt gcc gaa gcg gag aag gat atc gat ccc atg ggt gct tgt ggg<br>Lys Val Ala Glu Ala Glu Lys Asp Ile Asp Pro Met Gly Ala Cys Gly<br>              500                   505                   510 | 1536 | |
| tcg aag gac tcg acg agc gac aag ggg ttg gcg agc gat aag gac ggc<br>Ser Lys Asp Ser Thr Ser Asp Lys Gly Leu Ala Ser Asp Lys Asp Gly<br>                   515                   520                   525 | 1584 | |
| aag aac gcc aag gac cgc aag gaa gcg tgg gag cgc att cgc cag gcg<br>Lys Asn Ala Lys Asp Arg Lys Glu Ala Trp Glu Arg Ile Arg Gln Ala<br>530                   535                   540 | 1632 | |
| att cct cgt gag aag acc gcc gag gca aaa cag cgc cgc atc gag ctc<br>Ile Pro Arg Glu Lys Thr Ala Glu Ala Lys Gln Arg Arg Ile Glu Leu<br>545                   550                   555                   560 | 1680 | |
| ttc aag aag ttc gac aag aac gag acc ggg aag ctg tgc tac gat gag<br>Phe Lys Lys Phe Asp Lys Asn Glu Thr Gly Lys Leu Cys Tyr Asp Glu<br>                   565                   570                   575 | 1728 | |
| gtg cac agc ggc tgc ctc gag gtg ctg aag ttg gac gag ttc acg ccg<br>Val His Ser Gly Cys Leu Glu Val Leu Lys Leu Asp Glu Phe Thr Pro<br>              580                   585                   590 | 1776 | |
| cga gtg cgc gac atc acg aag cgt gca ttc gac aag gcg agg gcc ctg | 1824 | |

```
Arg Val Arg Asp Ile Thr Lys Arg Ala Phe Asp Lys Ala Arg Ala Leu
        595                 600                 605 ggc agc aag ctg gag aac aag ggc tcc gag gac ttt gtt gaa ttt ctg    1872
Gly Ser Lys Leu Glu Asn Lys Gly Ser Glu Asp Phe Val Glu Phe Leu
610                 615                 620 gag ttc cgt ctg atg ctg tgc tac atc tac gac ttc ttc gag ctg acg    1920
Glu Phe Arg Leu Met Leu Cys Tyr Ile Tyr Asp Phe Phe Glu Leu Thr
625                 630                 635                 640 gtg atg ttc gac gag att gac gcc tcc ggc aac atg ctg gtt gac gag    1968
Val Met Phe Asp Glu Ile Asp Ala Ser Gly Asn Met Leu Val Asp Glu
                645                 650                 655 gag gag ttc aag cgc gcc gtg ccc aag ctt gag gcg tgg ggc gcc aag    2016
Glu Glu Phe Lys Arg Ala Val Pro Lys Leu Glu Ala Trp Gly Ala Lys
                660                 665                 670 gtc gag gat ccc gcg gcg ctg ttc aag gag ctc gat aag aac ggc act    2064
Val Glu Asp Pro Ala Ala Leu Phe Lys Glu Leu Asp Lys Asn Gly Thr
                675                 680                 685 ggg tcc gtg acg ttc gac gag ttt gct gcg tgg gct tct gca gtc aaa    2112
Gly Ser Val Thr Phe Asp Glu Phe Ala Ala Trp Ala Ser Ala Val Lys
690                 695                 700 ctg gac gcc gac ggc gac ccg gac aac gtg ccg gat atc                2151
Leu Asp Ala Asp Gly Asp Pro Asp Asn Val Pro Asp Ile
705                 710                 715

<210> SEQ ID NO 36
<211> LENGTH: 717
<212> TYPE: PRT
<213> ORGANISM: Trypanosoma cruzi

<400> SEQUENCE: 36

Met Ala Arg Ala Val Val Leu Glu Asp Gly Ala Leu Tyr Val Ala Asp
  1               5                  10                  15

Asn Ala Asn Asn Leu Val Arg Glu Ile Ser Asn Gly Val Val Thr Ser
                 20                  25                  30

Phe Ile Thr Glu Gly Leu Leu Gly Pro Ser Tyr Ile Lys Pro Tyr Ser
             35                  40                  45

Arg Thr Asn Gly Ala His Asp Leu Phe Val Ser Asp Thr Gly Lys Ser
         50                  55                  60

Arg Ile Ile Phe Ala Pro Pro Gln Lys Lys Thr Phe Ile Thr Val Phe
 65                  70                  75                  80

Ile Thr Gly Phe Gln Pro Asp Val Leu Gln Ile Ser Glu Lys Ser Arg
                 85                  90                  95

Leu Met Phe Ala Ile Cys Asn Ser Thr Lys Ile Leu Ala Ile Asn Met
                100                 105                 110

Gln Gly Ala Thr Thr Pro Lys Glu Tyr Trp Gln Val Gly Asn Ala Asp
            115                 120                 125

Cys Met Gly Tyr Gln Ser Ser Leu Met Leu Thr Thr Glu Glu Asp Lys
        130                 135                 140

Leu Leu Tyr Tyr Gly Ile Leu Asn Gly Thr Pro Ser Ile Met Ser Leu
145                 150                 155                 160

Pro Ala Thr Lys Thr Lys Thr Glu Ala Pro Arg Ile Cys Pro Asp Val
                165                 170                 175

Leu Leu Gln Trp Pro His Gly Pro Ile Val Ser Leu Val Asn Ile Asn
            180                 185                 190

Lys His Ala Phe Tyr Val Val Thr Ala Ser Asn Val Tyr Ile Val His
        195                 200                 205

Asp Gly Ser Tyr His Pro Thr Gly Ser Met Ala Gln Leu Gln Gln Ala
    210                 215                 220
```

```
Glu Asn Asn Ile Thr Asn Ser Lys Lys Glu Met Thr Lys Leu Arg Glu
225                 230                 235                 240

Lys Val Lys Lys Ala Glu Lys Glu Lys Leu Asp Ala Ile Asn Arg Ala
            245                 250                 255

Thr Lys Leu Glu Glu Arg Asn Gln Ala Tyr Lys Ala Ala His Lys
        260                 265                 270

Ala Glu Glu Lys Ala Lys Thr Phe Gln Arg Leu Ile Thr Phe Glu
    275                 280                 285

Ser Glu Asn Ile Asn Leu Lys Lys Arg Pro Asn Asp Ala Val Ser Asn
290                 295                 300

Arg Asp Lys Lys Lys Asn Ser Glu Thr Ala Lys Thr Asp Glu Val Glu
305                 310                 315                 320

Lys Gln Arg Ala Ala Glu Ala Ala Lys Ala Val Glu Thr Glu Lys Gln
                325                 330                 335

Arg Ala Ala Glu Ala Thr Lys Val Ala Glu Ala Glu Lys Arg Lys Ala
                340                 345                 350

Ala Glu Ala Ala Lys Ala Val Glu Thr Glu Lys Gln Arg Ala Ala Glu
            355                 360                 365

Ala Thr Lys Val Ala Glu Ala Glu Lys Gln Lys Ala Ala Glu Ala Ala
    370                 375                 380

Lys Ala Val Glu Thr Glu Lys Gln Arg Ala Ala Glu Ala Thr Lys Val
385                 390                 395                 400

Ala Glu Ala Glu Lys Gln Arg Ala Ala Glu Ala Met Lys Val Ala Glu
                405                 410                 415

Ala Glu Lys Gln Lys Ala Ala Glu Ala Ala Lys Ala Val Glu Thr Glu
                420                 425                 430

Lys Gln Arg Ala Ala Glu Ala Thr Lys Val Ala Glu Ala Glu Lys Gln
                435                 440                 445

Lys Ala Ala Glu Ala Ala Lys Ala Val Glu Thr Glu Lys Gln Arg Ala
            450                 455                 460

Ala Glu Ala Thr Lys Val Ala Glu Ala Glu Lys Gln Lys Ala Ala Glu
465                 470                 475                 480

Ala Ala Lys Ala Val Glu Thr Glu Lys Gln Arg Ala Ala Glu Ala Thr
                485                 490                 495

Lys Val Ala Glu Ala Glu Lys Asp Ile Asp Pro Met Gly Ala Cys Gly
                500                 505                 510

Ser Lys Asp Ser Thr Ser Asp Lys Gly Leu Ala Ser Asp Lys Asp Gly
        515                 520                 525

Lys Asn Ala Lys Asp Arg Lys Glu Ala Trp Glu Arg Ile Arg Gln Ala
    530                 535                 540

Ile Pro Arg Glu Lys Thr Ala Glu Ala Lys Gln Arg Ile Glu Leu
545                 550                 555                 560

Phe Lys Lys Phe Asp Lys Asn Glu Thr Gly Lys Leu Cys Tyr Asp Glu
                565                 570                 575

Val His Ser Gly Cys Leu Glu Val Leu Lys Leu Asp Glu Phe Thr Pro
            580                 585                 590

Arg Val Arg Asp Ile Thr Lys Arg Ala Phe Asp Lys Ala Arg Ala Leu
        595                 600                 605

Gly Ser Lys Leu Glu Asn Lys Gly Ser Glu Asp Phe Val Glu Phe Leu
    610                 615                 620

Glu Phe Arg Leu Met Leu Cys Tyr Ile Tyr Asp Phe Phe Glu Leu Thr
625                 630                 635                 640

Val Met Phe Asp Glu Ile Asp Ala Ser Gly Asn Met Leu Val Asp Glu
```

```
                                    645                 650                 655
Glu Glu Phe Lys Arg Ala Val Pro Lys Leu Glu Ala Trp Gly Ala Lys
            660                 665                 670

Val Glu Asp Pro Ala Ala Leu Phe Lys Glu Leu Asp Lys Asn Gly Thr
            675                 680                 685

Gly Ser Val Thr Phe Asp Glu Phe Ala Ala Trp Ala Ser Ala Val Lys
            690                 695                 700

Leu Asp Ala Asp Gly Asp Pro Asp Asn Val Pro Asp Ile
705                 710                 715

<210> SEQ ID NO 37
<211> LENGTH: 1836
<212> TYPE: DNA
<213> ORGANISM: Trypanosoma cruzi
<220> FEATURE:
<221> NAME/KEY: CDS
<222> LOCATION: (1)..(1836)

<400> SEQUENCE: 37 atg gag cag gag cgc agg cag ctg ctc gag aag gac ccg cgc agg aac     48
Met Glu Gln Glu Arg Arg Gln Leu Leu Glu Lys Asp Pro Arg Arg Asn
 1               5                  10                  15 gcg aag gag atc gct gcg ctt gag gag agc atg aat gcc cgc gca cag     96
Ala Lys Glu Ile Ala Ala Leu Glu Glu Ser Met Asn Ala Arg Ala Gln
            20                  25                  30 gag ctg gca cgc gag aag aag ctt gct gac cgc gcg ttc ctc gac cag    144
Glu Leu Ala Arg Glu Lys Lys Leu Ala Asp Arg Ala Phe Leu Asp Gln
        35                  40                  45 aag ccg gag ggc gtg ccg ctg cga gag ctg ccg ctc gac gac gac agc    192
Lys Pro Glu Gly Val Pro Leu Arg Glu Leu Pro Leu Asp Asp Asp Ser
    50                  55                  60 gac ttt gtt gct atg gag cag gag cgc agg cag ctg ctc gag aag gac    240
Asp Phe Val Ala Met Glu Gln Glu Arg Arg Gln Leu Leu Glu Lys Asp
65                  70                  75                  80 ccg cgc agg aac gcg aag gag atc gct gcg ctt gag gag agc atg aat    288
Pro Arg Arg Asn Ala Lys Glu Ile Ala Ala Leu Glu Glu Ser Met Asn
                85                  90                  95 gcc cgc gca cag gag ctg gca cgc gag aag aag ctt gct gac cgc gcg    336
Ala Arg Ala Gln Glu Leu Ala Arg Glu Lys Lys Leu Ala Asp Arg Ala
            100                 105                 110 ttc ctc gac cag aag ccg gag ggc gtg ccg ctg cga gag ctg ccg ctc    384
Phe Leu Asp Gln Lys Pro Glu Gly Val Pro Leu Arg Glu Leu Pro Leu
        115                 120                 125 gac gac gac agc gac ttt gtt gct atg gag cag gag cgc agg cag ctg    432
Asp Asp Asp Ser Asp Phe Val Ala Met Glu Gln Glu Arg Arg Gln Leu
    130                 135                 140 ctc gag aag gac ccg cgc agg aac gcg aag gag atc gct gcg ctt gag    480
Leu Glu Lys Asp Pro Arg Arg Asn Ala Lys Glu Ile Ala Ala Leu Glu
145                 150                 155                 160 gag agc atg aat gcc cgc gca cag gag ctg gca cgc gag aag aag ctt    528
Glu Ser Met Asn Ala Arg Ala Gln Glu Leu Ala Arg Glu Lys Lys Leu
                165                 170                 175 gct gac cgc gcg ttc ctc gac cag aag ccg gag ggc gtg ccg ctg cga    576
Ala Asp Arg Ala Phe Leu Asp Gln Lys Pro Glu Gly Val Pro Leu Arg
            180                 185                 190 gag ctg ccg ctc gac gac gac agc gac ttt gtt gct atg gag cag gag    624
Glu Leu Pro Leu Asp Asp Asp Ser Asp Phe Val Ala Met Glu Gln Glu
        195                 200                 205 cgc agg cag ctg ctc gag aag gac ccg cgc agg aac gcg aag gag atc    672
Arg Arg Gln Leu Leu Glu Lys Asp Pro Arg Arg Asn Ala Lys Glu Ile
    210                 215                 220
```

| | | |
|---|---|---|
| gct gcg ctt gag gag agc atg aat gcc cgc gca cag gag ctg gca cgc<br>Ala Ala Leu Glu Glu Ser Met Asn Ala Arg Ala Gln Glu Leu Ala Arg<br>225                    230                    235                    240 | 720 |
| gag aag aag ctt gct gac cgc gcg ttc ctc gac cag aag ccg gag ggc<br>Glu Lys Lys Leu Ala Asp Arg Ala Phe Leu Asp Gln Lys Pro Glu Gly<br>                    245                    250                    255 | 768 |
| gtg ccg ctg cga gag ctg ccg ctc gac gac gac agc gac ttt gtt gct<br>Val Pro Leu Arg Glu Leu Pro Leu Asp Asp Asp Ser Asp Phe Val Ala<br>        260                    265                    270 | 816 |
| atg gag cag gag cgc agg cag ctg ctc gag aag gac ccg cgc agg aac<br>Met Glu Gln Glu Arg Arg Gln Leu Leu Glu Lys Asp Pro Arg Arg Asn<br>275                    280                    285 | 864 |
| gcg aag gag atc gct gcg ctt gag gag agc atg aat gcc cgc gca cag<br>Ala Lys Glu Ile Ala Ala Leu Glu Glu Ser Met Asn Ala Arg Ala Gln<br>        290                    295                    300 | 912 |
| gag ctg gca cgc gag aag aag ctt gct gac cgc gcg ttc ctc gac cag<br>Glu Leu Ala Arg Glu Lys Lys Leu Ala Asp Arg Ala Phe Leu Asp Gln<br>305                    310                    315                    320 | 960 |
| aag ccg gag ggc gtg ccg ctg cga gag ctg ccg ctc gac gac gac agc<br>Lys Pro Glu Gly Val Pro Leu Arg Glu Leu Pro Leu Asp Asp Asp Ser<br>                    325                    330                    335 | 1008 |
| gac ttt gtt gct atg gag cag gag cgc agg cag ctg ctc gag aag gac<br>Asp Phe Val Ala Met Glu Gln Glu Arg Arg Gln Leu Leu Glu Lys Asp<br>        340                    345                    350 | 1056 |
| ccg cgc agg aac gcg aag gag atc gct gcg ctt gag gag agc atg aat<br>Pro Arg Arg Asn Ala Lys Glu Ile Ala Ala Leu Glu Glu Ser Met Asn<br>355                    360                    365 | 1104 |
| gcc cgc gca cag gag ctg gca cgc gag aag aag ctt gct gac cgc gcg<br>Ala Arg Ala Gln Glu Leu Ala Arg Glu Lys Lys Leu Ala Asp Arg Ala<br>        370                    375                    380 | 1152 |
| ttc ctc gac cag aag ccg gag ggc gtg ccg ctg cga gag ctg ccg ctc<br>Phe Leu Asp Gln Lys Pro Glu Gly Val Pro Leu Arg Glu Leu Pro Leu<br>385                    390                    395                    400 | 1200 |
| gac gac gac agc gac ttt gtt gct atg gag cag gag cgc agg cag ctg<br>Asp Asp Asp Ser Asp Phe Val Ala Met Glu Gln Glu Arg Arg Gln Leu<br>                    405                    410                    415 | 1248 |
| ctc gag aag gac ccg cgc agg aac gcg aag gag atc gct gcg ctt gag<br>Leu Glu Lys Asp Pro Arg Arg Asn Ala Lys Glu Ile Ala Ala Leu Glu<br>        420                    425                    430 | 1296 |
| gag agc atg aat gcc cgc gca cag gag ctg gca cgc gag aag aag ctt<br>Glu Ser Met Asn Ala Arg Ala Gln Glu Leu Ala Arg Glu Lys Lys Leu<br>435                    440                    445 | 1344 |
| gct gac cgc gcg ttc ctc gac cag aag ccg gag ggc gtg ccg ctg cga<br>Ala Asp Arg Ala Phe Leu Asp Gln Lys Pro Glu Gly Val Pro Leu Arg<br>        450                    455                    460 | 1392 |
| gag ctg ccg ctc gac gac gac agc gac ttt gtt gct atg gag cag gag<br>Glu Leu Pro Leu Asp Asp Asp Ser Asp Phe Val Ala Met Glu Gln Glu<br>465                    470                    475                    480 | 1440 |
| cgc agg cag ctg ctc gag aag gac ccg cgc agg aac gcg aag gag atc<br>Arg Arg Gln Leu Leu Glu Lys Asp Pro Arg Arg Asn Ala Lys Glu Ile<br>                    485                    490                    495 | 1488 |
| gct gcg ctt gag gag agc atg aat gcc cgc gca cag gag ctg gca cgc<br>Ala Ala Leu Glu Glu Ser Met Asn Ala Arg Ala Gln Glu Leu Ala Arg<br>        500                    505                    510 | 1536 |
| gag aag aag ctt gct gac cgc gcg ttc ctc gac cag aag ccg gag ggc<br>Glu Lys Lys Leu Ala Asp Arg Ala Phe Leu Asp Gln Lys Pro Glu Gly<br>                    515                    520                    525 | 1584 |
| gtg ccg ctg cga gag ctg ccg ctc gac gac gac agc gac ttt gtt gct<br>Val Pro Leu Arg Glu Leu Pro Leu Asp Asp Asp Ser Asp Phe Val Ala<br>        530                    535                    540 | 1632 |

```
atg gag cag gag cgc agg cag ctg ctc gag aag gac ccg cgc agg aac    1680
Met Glu Gln Glu Arg Arg Gln Leu Leu Glu Lys Asp Pro Arg Arg Asn
545                 550                 555                 560 gcg aag gag atc gct gcg ctt gag gag agc atg aat gcc cgc gca cag    1728
Ala Lys Glu Ile Ala Ala Leu Glu Glu Ser Met Asn Ala Arg Ala Gln
            565                 570                 575 gag ctg gca cgc gag aag aag ctt gct gac cgc gcg ttc ctc gac cag    1776
Glu Leu Ala Arg Glu Lys Lys Leu Ala Asp Arg Ala Phe Leu Asp Gln
        580                 585                 590 aag ccg gag ggc gtg ccg ctg cga gag ctg ccg ctc gac gac gac agc    1824
Lys Pro Glu Gly Val Pro Leu Arg Glu Leu Pro Leu Asp Asp Asp Ser
    595                 600                 605 gac ttt gtt gct                                                    1836
Asp Phe Val Ala
    610
```

<210> SEQ ID NO 38
<211> LENGTH: 612
<212> TYPE: PRT
<213> ORGANISM: Trypanosoma cruzi

<400> SEQUENCE: 38

```
Met Glu Gln Glu Arg Arg Gln Leu Leu Glu Lys Asp Pro Arg Arg Asn
 1               5                  10                  15

Ala Lys Glu Ile Ala Ala Leu Glu Glu Ser Met Asn Ala Arg Ala Gln
            20                  25                  30

Glu Leu Ala Arg Glu Lys Lys Leu Ala Asp Arg Ala Phe Leu Asp Gln
        35                  40                  45

Lys Pro Glu Gly Val Pro Leu Arg Glu Leu Pro Leu Asp Asp Asp Ser
    50                  55                  60

Asp Phe Val Ala Met Glu Gln Glu Arg Arg Gln Leu Leu Glu Lys Asp
65                  70                  75                  80

Pro Arg Arg Asn Ala Lys Glu Ile Ala Ala Leu Glu Glu Ser Met Asn
                85                  90                  95

Ala Arg Ala Gln Glu Leu Ala Arg Glu Lys Lys Leu Ala Asp Arg Ala
            100                 105                 110

Phe Leu Asp Gln Lys Pro Glu Gly Val Pro Leu Arg Glu Leu Pro Leu
        115                 120                 125

Asp Asp Asp Ser Asp Phe Val Ala Met Glu Gln Glu Arg Arg Gln Leu
    130                 135                 140

Leu Glu Lys Asp Pro Arg Arg Asn Ala Lys Glu Ile Ala Ala Leu Glu
145                 150                 155                 160

Glu Ser Met Asn Ala Arg Ala Gln Glu Leu Ala Arg Glu Lys Lys Leu
                165                 170                 175

Ala Asp Arg Ala Phe Leu Asp Gln Lys Pro Glu Gly Val Pro Leu Arg
            180                 185                 190

Glu Leu Pro Leu Asp Asp Asp Ser Asp Phe Val Ala Met Glu Gln Glu
        195                 200                 205

Arg Arg Gln Leu Leu Glu Lys Asp Pro Arg Arg Asn Ala Lys Glu Ile
    210                 215                 220

Ala Ala Leu Glu Glu Ser Met Asn Ala Arg Ala Gln Glu Leu Ala Arg
225                 230                 235                 240

Glu Lys Lys Leu Ala Asp Arg Ala Phe Leu Asp Gln Lys Pro Glu Gly
                245                 250                 255

Val Pro Leu Arg Glu Leu Pro Leu Asp Asp Asp Ser Asp Phe Val Ala
            260                 265                 270
```

```
Met Glu Gln Glu Arg Arg Gln Leu Leu Glu Lys Asp Pro Arg Arg Asn
    275                 280                 285

Ala Lys Glu Ile Ala Ala Leu Glu Glu Ser Met Asn Ala Arg Ala Gln
    290                 295                 300

Glu Leu Ala Arg Glu Lys Lys Leu Ala Asp Arg Ala Phe Leu Asp Gln
305                 310                 315                 320

Lys Pro Glu Gly Val Pro Leu Arg Glu Leu Pro Leu Asp Asp Asp Ser
                325                 330                 335

Asp Phe Val Ala Met Glu Gln Glu Arg Arg Gln Leu Leu Glu Lys Asp
                340                 345                 350

Pro Arg Arg Asn Ala Lys Glu Ile Ala Ala Leu Glu Glu Ser Met Asn
            355                 360                 365

Ala Arg Ala Gln Glu Leu Ala Arg Glu Lys Lys Leu Ala Asp Arg Ala
    370                 375                 380

Phe Leu Asp Gln Lys Pro Glu Gly Val Pro Leu Arg Glu Leu Pro Leu
385                 390                 395                 400

Asp Asp Asp Ser Asp Phe Val Ala Met Glu Gln Glu Arg Arg Gln Leu
                405                 410                 415

Leu Glu Lys Asp Pro Arg Arg Asn Ala Lys Glu Ile Ala Ala Leu Glu
            420                 425                 430

Glu Ser Met Asn Ala Arg Ala Gln Glu Leu Ala Arg Glu Lys Lys Leu
    435                 440                 445

Ala Asp Arg Ala Phe Leu Asp Gln Lys Pro Glu Gly Val Pro Leu Arg
    450                 455                 460

Glu Leu Pro Leu Asp Asp Asp Ser Asp Phe Val Ala Met Glu Gln Glu
465                 470                 475                 480

Arg Arg Gln Leu Leu Glu Lys Asp Pro Arg Arg Asn Ala Lys Glu Ile
                485                 490                 495

Ala Ala Leu Glu Glu Ser Met Asn Ala Arg Ala Gln Glu Leu Ala Arg
            500                 505                 510

Glu Lys Lys Leu Ala Asp Arg Ala Phe Leu Asp Gln Lys Pro Glu Gly
    515                 520                 525

Val Pro Leu Arg Glu Leu Pro Leu Asp Asp Asp Ser Asp Phe Val Ala
    530                 535                 540

Met Glu Gln Glu Arg Arg Gln Leu Leu Glu Lys Asp Pro Arg Arg Asn
545                 550                 555                 560

Ala Lys Glu Ile Ala Ala Leu Glu Glu Ser Met Asn Ala Arg Ala Gln
                565                 570                 575

Glu Leu Ala Arg Glu Lys Lys Leu Ala Asp Arg Ala Phe Leu Asp Gln
            580                 585                 590

Lys Pro Glu Gly Val Pro Leu Arg Glu Leu Pro Leu Asp Asp Asp Ser
    595                 600                 605

Asp Phe Val Ala
    610

<210> SEQ ID NO 39
<211> LENGTH: 621
<212> TYPE: DNA
<213> ORGANISM: Trypanosoma cruzi
<220> FEATURE:
<221> NAME/KEY: CDS
<222> LOCATION: (1)..(621)

<400> SEQUENCE: 39 ttt aat cct tct acg gac aaa ttg aag cta aac caa caa aat aag cct    48
Phe Asn Pro Ser Thr Asp Lys Leu Lys Leu Asn Gln Gln Asn Lys Pro
  1               5                  10                  15
```

```
cat att gca aat aat aaa caa aaa aca aca ctc gaa aaa act caa aca      96
His Ile Ala Asn Asn Lys Gln Lys Thr Thr Leu Glu Lys Thr Gln Thr
         20                  25                  30 gaa caa aaa aca gcg cca ttt gga cag ggc gca gca ggg tgg aca aaa     144
Glu Gln Lys Thr Ala Pro Phe Gly Gln Gly Ala Ala Gly Trp Thr Lys
         35                  40                  45 cca tca cca ttt gga cag gcc gca gca ggt gac aaa cca cca cca ttt     192
Pro Ser Pro Phe Gly Gln Ala Ala Ala Gly Asp Lys Pro Pro Pro Phe
 50                  55                  60 gga cag gcc gca gca ggt gac aaa cca cca cca ttt gga cag gcc gca     240
Gly Gln Ala Ala Ala Gly Asp Lys Pro Pro Pro Phe Gly Gln Ala Ala
 65                  70                  75                  80 gca ggt gac aaa cca tca cta ttt gga cag gcc gca gca ggt gac aaa     288
Ala Gly Asp Lys Pro Ser Leu Phe Gly Gln Ala Ala Ala Gly Asp Lys
                 85                  90                  95 cca tca cca ttt gga cag gcc gca gca ggt gac aaa cca cca cca ttt     336
Pro Ser Pro Phe Gly Gln Ala Ala Ala Gly Asp Lys Pro Pro Pro Phe
            100                 105                 110 gga cag gcc gca gca ggt gac aaa cca tca cta ttt gga cag gcc gca     384
Gly Gln Ala Ala Ala Gly Asp Lys Pro Ser Leu Phe Gly Gln Ala Ala
        115                 120                 125 gca ggt gac aaa cca tca cca ttt gga cag gcc gca gca ggt gac aaa     432
Ala Gly Asp Lys Pro Ser Pro Phe Gly Gln Ala Ala Ala Gly Asp Lys
    130                 135                 140 cca cca cca ttt gga cag gcc gca gca ggt gac aaa cca cca cca ttt     480
Pro Pro Pro Phe Gly Gln Ala Ala Ala Gly Asp Lys Pro Pro Pro Phe
145                 150                 155                 160 gga cag gcc gca gca ggt gac aaa cca tca cta ttt gga cag gcc gca     528
Gly Gln Ala Ala Ala Gly Asp Lys Pro Ser Leu Phe Gly Gln Ala Ala
            165                 170                 175 gca ggt gac aaa cca tca cca ttt gga cag gga act gcg ttt gat gcc     576
Ala Gly Asp Lys Pro Ser Pro Phe Gly Gln Gly Thr Ala Phe Asp Ala
        180                 185                 190 tct cga agc act gtg ttt gcg aat gcg cct ggt gtt gcc cag gtg         621
Ser Arg Ser Thr Val Phe Ala Asn Ala Pro Gly Val Ala Gln Val
    195                 200                 205

<210> SEQ ID NO 40
<211> LENGTH: 207
<212> TYPE: PRT
<213> ORGANISM: Trypanosoma cruzi

<400> SEQUENCE: 40

Phe Asn Pro Ser Thr Asp Lys Leu Lys Leu Asn Gln Gln Asn Lys Pro
 1               5                  10                  15

His Ile Ala Asn Asn Lys Gln Lys Thr Thr Leu Glu Lys Thr Gln Thr
             20                  25                  30

Glu Gln Lys Thr Ala Pro Phe Gly Gln Gly Ala Ala Gly Trp Thr Lys
         35                  40                  45

Pro Ser Pro Phe Gly Gln Ala Ala Ala Gly Asp Lys Pro Pro Pro Phe
     50                  55                  60

Gly Gln Ala Ala Ala Gly Asp Lys Pro Pro Pro Phe Gly Gln Ala Ala
 65                  70                  75                  80

Ala Gly Asp Lys Pro Ser Leu Phe Gly Gln Ala Ala Ala Gly Asp Lys
                 85                  90                  95

Pro Ser Pro Phe Gly Gln Ala Ala Ala Gly Asp Lys Pro Pro Pro Phe
            100                 105                 110

Gly Gln Ala Ala Ala Gly Asp Lys Pro Ser Leu Phe Gly Gln Ala Ala
        115                 120                 125
```

```
Ala Gly Asp Lys Pro Ser Pro Phe Gly Gln Ala Ala Gly Asp Lys
        130                 135                 140

Pro Pro Pro Phe Gly Gln Ala Ala Gly Asp Lys Pro Pro Phe
145                 150                 155                 160

Gly Gln Ala Ala Ala Gly Asp Lys Pro Ser Leu Phe Gly Gln Ala Ala
                165                 170                 175

Ala Gly Asp Lys Pro Ser Pro Phe Gly Gln Gly Thr Ala Phe Asp Ala
            180                 185                 190

Ser Arg Ser Thr Val Phe Ala Asn Ala Pro Gly Val Ala Gln Val
        195                 200                 205

<210> SEQ ID NO 41
<211> LENGTH: 1845
<212> TYPE: DNA
<213> ORGANISM: Trypanosoma cruzi
<220> FEATURE:
<221> NAME/KEY: CDS
<222> LOCATION: (1)..(1845)

<400> SEQUENCE: 41
```

| | | | | | | | | | | | | | | | | |
|---|---|---|---|---|---|---|---|---|---|---|---|---|---|---|---|---|
| ttt | aat | cct | tct | acg | gac | aaa | ttg | aag | cta | aac | caa | caa | aat | aag | cct | 48 |
| Phe | Asn | Pro | Ser | Thr | Asp | Lys | Leu | Lys | Leu | Asn | Gln | Gln | Asn | Lys | Pro | |
| 1 | | | | 5 | | | | | 10 | | | | | 15 | | |
| cat | att | gca | aat | aat | aaa | caa | aaa | aca | aca | ctc | gaa | aaa | act | caa | aca | 96 |
| His | Ile | Ala | Asn | Asn | Lys | Gln | Lys | Thr | Thr | Leu | Glu | Lys | Thr | Gln | Thr | |
| | | | | 20 | | | | | 25 | | | | | 30 | | |
| gaa | caa | aaa | aca | gcg | cca | ttt | gga | cag | ggc | gca | gca | ggg | tgg | aca | aaa | 144 |
| Glu | Gln | Lys | Thr | Ala | Pro | Phe | Gly | Gln | Gly | Ala | Ala | Gly | Trp | Thr | Lys | |
| | | 35 | | | | | 40 | | | | | 45 | | | | |
| cca | tca | cca | ttt | gga | cag | gcc | gca | gca | ggt | gac | aaa | cca | cca | cca | ttt | 192 |
| Pro | Ser | Pro | Phe | Gly | Gln | Ala | Ala | Ala | Gly | Asp | Lys | Pro | Pro | Pro | Phe | |
| 50 | | | | | 55 | | | | | 60 | | | | | | |
| gga | cag | gcc | gca | gca | ggt | gac | aaa | cca | cca | cca | ttt | gga | cag | gcc | gca | 240 |
| Gly | Gln | Ala | Ala | Ala | Gly | Asp | Lys | Pro | Pro | Pro | Phe | Gly | Gln | Ala | Ala | |
| 65 | | | | | 70 | | | | | 75 | | | | | 80 | |
| gca | ggt | gac | aaa | cca | tca | cta | ttt | gga | cag | gcc | gca | gca | ggt | gac | aaa | 288 |
| Ala | Gly | Asp | Lys | Pro | Ser | Leu | Phe | Gly | Gln | Ala | Ala | Ala | Gly | Asp | Lys | |
| | | | | 85 | | | | | 90 | | | | | 95 | | |
| cca | tca | cca | ttt | gga | cag | gcc | gca | gca | ggt | gac | aaa | cca | cca | cca | ttt | 336 |
| Pro | Ser | Pro | Phe | Gly | Gln | Ala | Ala | Ala | Gly | Asp | Lys | Pro | Pro | Pro | Phe | |
| | | | | 100 | | | | | 105 | | | | | 110 | | |
| gga | cag | gcc | gca | gca | ggt | gac | aaa | cca | tca | cta | ttt | gga | cag | gcc | gca | 384 |
| Gly | Gln | Ala | Ala | Ala | Gly | Asp | Lys | Pro | Ser | Leu | Phe | Gly | Gln | Ala | Ala | |
| | | | 115 | | | | | 120 | | | | | 125 | | | |
| gca | ggt | gac | aaa | cca | tca | cca | ttt | gga | cag | gcc | gca | gca | ggt | gac | aaa | 432 |
| Ala | Gly | Asp | Lys | Pro | Ser | Pro | Phe | Gly | Gln | Ala | Ala | Ala | Gly | Asp | Lys | |
| | | | 130 | | | | | 135 | | | | | 140 | | | |
| cca | cca | cca | ttt | gga | cag | gcc | gca | gca | ggt | gac | aaa | cca | cca | cca | ttt | 480 |
| Pro | Pro | Pro | Phe | Gly | Gln | Ala | Ala | Ala | Gly | Asp | Lys | Pro | Pro | Pro | Phe | |
| 145 | | | | | 150 | | | | | 155 | | | | | 160 | |
| gga | cag | gcc | gca | gca | ggt | gac | aaa | cca | tca | cta | ttt | gga | cag | gcc | gca | 528 |
| Gly | Gln | Ala | Ala | Ala | Gly | Asp | Lys | Pro | Ser | Leu | Phe | Gly | Gln | Ala | Ala | |
| | | | 165 | | | | | 170 | | | | | 175 | | | |
| gca | ggt | gac | aaa | cca | tca | cca | ttt | gga | cag | gga | act | gcg | ttt | gat | gcc | 576 |
| Ala | Gly | Asp | Lys | Pro | Ser | Pro | Phe | Gly | Gln | Gly | Thr | Ala | Phe | Asp | Ala | |
| | | | 180 | | | | | 185 | | | | | 190 | | | |
| tct | cga | agc | act | gtg | ttt | gcg | aat | gcg | cct | ggt | gtt | gcc | cag | gtg | atg | 624 |
| Ser | Arg | Ser | Thr | Val | Phe | Ala | Asn | Ala | Pro | Gly | Val | Ala | Gln | Val | Met | |
| | | | 195 | | | | | 200 | | | | | 205 | | | |
| gag | cag | gag | cgc | agg | cag | ctg | ctc | gag | aag | gac | ccg | cgc | agg | aac | gcg | 672 |

```
                    -continued

Glu Gln Glu Arg Arg Gln Leu Leu Glu Lys Asp Pro Arg Arg Asn Ala
    210                 215                 220 aag gag atc gct gcg ctt gag gag agc atg aat gcc cgc gca cag gag        720
Lys Glu Ile Ala Ala Leu Glu Glu Ser Met Asn Ala Arg Ala Gln Glu
225                 230                 235                 240 ctg gca cgc gag aag aag ctt gct gac cgc gcg ttc ctc gac cag aag        768
Leu Ala Arg Glu Lys Lys Leu Ala Asp Arg Ala Phe Leu Asp Gln Lys
                245                 250                 255 ccg gag ggc gtg ccg ctg cga gag ctg ccg ctc gac gac gac agc gac        816
Pro Glu Gly Val Pro Leu Arg Glu Leu Pro Leu Asp Asp Asp Ser Asp
                    260                 265                 270 ttt gtt gct atg gag cag gag cgc agg cag ctg ctc gag aag gac ccg        864
Phe Val Ala Met Glu Gln Glu Arg Arg Gln Leu Leu Glu Lys Asp Pro
                275                 280                 285 cgc agg aac gcg aag gag atc gct gcg ctt gag gag agc atg aat gcc        912
Arg Arg Asn Ala Lys Glu Ile Ala Ala Leu Glu Glu Ser Met Asn Ala
        290                 295                 300 cgc gca cag gag ctg gca cgc gag aag aag ctt gct gac cgc gcg ttc        960
Arg Ala Gln Glu Leu Ala Arg Glu Lys Lys Leu Ala Asp Arg Ala Phe
305                 310                 315                 320 ctc gac cag aag ccg gag ggc gtg ccg ctg cga gag ctg ccg ctc gac       1008
Leu Asp Gln Lys Pro Glu Gly Val Pro Leu Arg Glu Leu Pro Leu Asp
                325                 330                 335 gac gac agc gac ttt gtt gct atg gag cag gag cgc agg cag ctg ctc       1056
Asp Asp Ser Asp Phe Val Ala Met Glu Gln Glu Arg Arg Gln Leu Leu
                340                 345                 350 gag aag gac ccg cgc agg aac gcg aag gag atc gct gcg ctt gag gag       1104
Glu Lys Asp Pro Arg Arg Asn Ala Lys Glu Ile Ala Ala Leu Glu Glu
                355                 360                 365 agc atg aat gcc cgc gca cag gag ctg gca cgc gag aag aag ctt gct       1152
Ser Met Asn Ala Arg Ala Gln Glu Leu Ala Arg Glu Lys Lys Leu Ala
370                 375                 380 gac cgc gcg ttc ctc gac cag aag ccg gag ggc gtg ccg ctg cga gag       1200
Asp Arg Ala Phe Leu Asp Gln Lys Pro Glu Gly Val Pro Leu Arg Glu
385                 390                 395                 400 ctg ccg ctc gac gac gac agc gac ttt gtt gct atg gag cag gag cgc       1248
Leu Pro Leu Asp Asp Asp Ser Asp Phe Val Ala Met Glu Gln Glu Arg
                405                 410                 415 agg cag ctg ctc gag aag gac ccg cgc agg aac gcg aag gag atc gct       1296
Arg Gln Leu Leu Glu Lys Asp Pro Arg Arg Asn Ala Lys Glu Ile Ala
                420                 425                 430 gcg ctt gag gag agc atg aat gcc cgc gca cag gag ctg gca cgc gag       1344
Ala Leu Glu Glu Ser Met Asn Ala Arg Ala Gln Glu Leu Ala Arg Glu
            435                 440                 445 aag aag ctt gct gac cgc gcg ttc ctc gac cag aag ccg gag ggc gtg       1392
Lys Lys Leu Ala Asp Arg Ala Phe Leu Asp Gln Lys Pro Glu Gly Val
450                 455                 460 ccg ctg cga gag ctg ccg ctc gac gac gac agc gac ttt gtt gct atg       1440
Pro Leu Arg Glu Leu Pro Leu Asp Asp Asp Ser Asp Phe Val Ala Met
465                 470                 475                 480 gag cag gag cgc agg cag ctg ctc gag aag gac ccg cgc agg aac gcg       1488
Glu Gln Glu Arg Arg Gln Leu Leu Glu Lys Asp Pro Arg Arg Asn Ala
                485                 490                 495 aag gag atc gct gcg ctt gag gag agc atg aat gcc cgc gca cag gag       1536
Lys Glu Ile Ala Ala Leu Glu Glu Ser Met Asn Ala Arg Ala Gln Glu
                500                 505                 510 ctg gca cgc gag aag aag ctt gct gac cgc gcg ttc ctc gac cag aag       1584
Leu Ala Arg Glu Lys Lys Leu Ala Asp Arg Ala Phe Leu Asp Gln Lys
                515                 520                 525 ccg gag ggc gtg ccg ctg cga gag ctg ccg ctc gac gac gac agc gac       1632
```

-continued

```
Pro Glu Gly Val Pro Leu Arg Glu Leu Pro Leu Asp Asp Ser Asp
        530                 535                 540 ttt gtt gct atg gag cag gag cgc agg cag ctg ctc gag aag gac ccg      1680
Phe Val Ala Met Glu Gln Glu Arg Arg Gln Leu Leu Glu Lys Asp Pro
545                 550                 555                 560 cgc agg aac gcg aag gag atc gct gcg ctt gag gag agc atg aat gcc      1728
Arg Arg Asn Ala Lys Glu Ile Ala Ala Leu Glu Glu Ser Met Asn Ala
                565                 570                 575 cgc gca cag gag ctg gca cgc gag aag aag ctt gct gac cgc gcg ttc      1776
Arg Ala Gln Glu Leu Ala Arg Glu Lys Lys Leu Ala Asp Arg Ala Phe
                580                 585                 590 ctc gac cag aag ccg gag ggc gtg ccg ctg cga gag ctg ccg ctc gac      1824
Leu Asp Gln Lys Pro Glu Gly Val Pro Leu Arg Glu Leu Pro Leu Asp
                595                 600                 605 gac gac agc gac ttt gtt gct                                          1845
Asp Asp Ser Asp Phe Val Ala
        610                 615
```

<210> SEQ ID NO 42
<211> LENGTH: 615
<212> TYPE: PRT
<213> ORGANISM: Trypanosoma cruzi

<400> SEQUENCE: 42

```
Phe Asn Pro Ser Thr Asp Lys Leu Lys Leu Asn Gln Gln Asn Lys Pro
1               5                   10                  15

His Ile Ala Asn Asn Lys Gln Lys Thr Thr Leu Glu Lys Thr Gln Thr
                20                  25                  30

Glu Gln Lys Thr Ala Pro Phe Gly Gln Gly Ala Ala Gly Trp Thr Lys
            35                  40                  45

Pro Ser Pro Phe Gly Gln Ala Ala Ala Gly Asp Lys Pro Pro Pro Phe
        50                  55                  60

Gly Gln Ala Ala Ala Gly Asp Lys Pro Pro Phe Gly Gln Ala Ala
65                  70                  75                  80

Ala Gly Asp Lys Pro Ser Leu Phe Gly Gln Ala Ala Gly Asp Lys
                85                  90                  95

Pro Ser Pro Phe Gly Gln Ala Ala Gly Asp Lys Pro Pro Pro Phe
            100                 105                 110

Gly Gln Ala Ala Ala Gly Asp Lys Pro Ser Leu Phe Gly Gln Ala Ala
        115                 120                 125

Ala Gly Asp Lys Pro Ser Pro Phe Gly Gln Ala Ala Gly Asp Lys
    130                 135                 140

Pro Pro Pro Phe Gly Gln Ala Ala Gly Asp Lys Pro Pro Pro Phe
145                 150                 155                 160

Gly Gln Ala Ala Ala Gly Asp Lys Pro Ser Leu Phe Gly Gln Ala Ala
                165                 170                 175

Ala Gly Asp Lys Pro Ser Pro Phe Gly Gln Gly Thr Ala Phe Asp Ala
            180                 185                 190

Ser Arg Ser Thr Val Phe Ala Asn Ala Pro Gly Val Ala Gln Val Met
        195                 200                 205

Glu Gln Glu Arg Arg Gln Leu Leu Lys Asp Pro Arg Arg Asn Ala
    210                 215                 220

Lys Glu Ile Ala Ala Leu Glu Glu Ser Met Asn Ala Arg Ala Gln Glu
225                 230                 235                 240

Leu Ala Arg Glu Lys Lys Leu Ala Asp Arg Ala Phe Leu Asp Gln Lys
                245                 250                 255

Pro Glu Gly Val Pro Leu Arg Glu Leu Pro Leu Asp Asp Ser Asp
```

```
                 260                 265                 270
    Phe Val Ala Met Glu Gln Glu Arg Arg Gln Leu Leu Glu Lys Asp Pro
            275                 280                 285

Arg Arg Asn Ala Lys Glu Ile Ala Ala Leu Glu Glu Ser Met Asn Ala
        290                 295                 300

Arg Ala Gln Glu Leu Ala Arg Glu Lys Lys Leu Ala Asp Arg Ala Phe
    305                 310                 315                 320

Leu Asp Gln Lys Pro Glu Gly Val Pro Leu Arg Glu Leu Pro Leu Asp
                    325                 330                 335

Asp Asp Ser Asp Phe Val Ala Met Glu Gln Glu Arg Arg Gln Leu Leu
                340                 345                 350

Glu Lys Asp Pro Arg Arg Asn Ala Lys Glu Ile Ala Ala Leu Glu Glu
            355                 360                 365

Ser Met Asn Ala Arg Ala Gln Glu Leu Ala Arg Glu Lys Lys Leu Ala
        370                 375                 380

Asp Arg Ala Phe Leu Asp Gln Lys Pro Glu Gly Val Pro Leu Arg Glu
    385                 390                 395                 400

Leu Pro Leu Asp Asp Asp Ser Asp Phe Val Ala Met Glu Gln Glu Arg
                    405                 410                 415

Arg Gln Leu Leu Glu Lys Asp Pro Arg Arg Asn Ala Lys Glu Ile Ala
                420                 425                 430

Ala Leu Glu Glu Ser Met Asn Ala Arg Ala Gln Glu Leu Ala Arg Glu
            435                 440                 445

Lys Lys Leu Ala Asp Arg Ala Phe Leu Asp Gln Lys Pro Glu Gly Val
        450                 455                 460

Pro Leu Arg Glu Leu Pro Leu Asp Asp Asp Ser Asp Phe Val Ala Met
    465                 470                 475                 480

Glu Gln Glu Arg Arg Gln Leu Leu Glu Lys Asp Pro Arg Arg Asn Ala
                    485                 490                 495

Lys Glu Ile Ala Ala Leu Glu Glu Ser Met Asn Ala Arg Ala Gln Glu
                500                 505                 510

Leu Ala Arg Glu Lys Lys Leu Ala Asp Arg Ala Phe Leu Asp Gln Lys
            515                 520                 525

Pro Glu Gly Val Pro Leu Arg Glu Leu Pro Leu Asp Asp Asp Ser Asp
        530                 535                 540

Phe Val Ala Met Glu Gln Glu Arg Arg Gln Leu Leu Glu Lys Asp Pro
    545                 550                 555                 560

Arg Arg Asn Ala Lys Glu Ile Ala Ala Leu Glu Glu Ser Met Asn Ala
                    565                 570                 575

Arg Ala Gln Glu Leu Ala Arg Glu Lys Lys Leu Ala Asp Arg Ala Phe
                580                 585                 590

Leu Asp Gln Lys Pro Glu Gly Val Pro Leu Arg Glu Leu Pro Leu Asp
            595                 600                 605

Asp Asp Ser Asp Phe Val Ala
        610                 615

<210> SEQ ID NO 43
<211> LENGTH: 858
<212> TYPE: DNA
<213> ORGANISM: Trypanosoma cruzi
<220> FEATURE:
<221> NAME/KEY: CDS
<222> LOCATION: (1)..(858)

<400> SEQUENCE: 43 gat cca acg tat cgt ttt gca aac cac gcg ttc acg ctg gtg gcg tcg          48
```

```
Asp Pro Thr Tyr Arg Phe Ala Asn His Ala Phe Thr Leu Val Ala Ser
 1               5                  10                  15 gtg acg att cac gag gtt ccg agc gtc gcg agt cct ttg ctg ggt gcg       96
Val Thr Ile His Glu Val Pro Ser Val Ala Ser Pro Leu Leu Gly Ala
             20                  25                  30 agc ctg gac tct tct ggt ggc aaa aaa ctc ctg ggg ctc tcg tac gac      144
Ser Leu Asp Ser Ser Gly Gly Lys Lys Leu Leu Gly Leu Ser Tyr Asp
         35                  40                  45 gag aag cac cag tgg cag cca ata tac gga tca acg ccg gtg acg ccg      192
Glu Lys His Gln Trp Gln Pro Ile Tyr Gly Ser Thr Pro Val Thr Pro
 50                  55                  60 acc gga tcg tgg gag atg ggt aag agg tac cac gtg gtt ctt acg atg      240
Thr Gly Ser Trp Glu Met Gly Lys Arg Tyr His Val Val Leu Thr Met
 65                  70                  75                  80 gcg aat aaa att ggc tcc gtg tac att gat gga gaa cct ctg gag ggt      288
Ala Asn Lys Ile Gly Ser Val Tyr Ile Asp Gly Glu Pro Leu Glu Gly
                 85                  90                  95 tca ggg cag acc gtt gtg cca gac gag agg acg cct gac atc tcc cac      336
Ser Gly Gln Thr Val Val Pro Asp Glu Arg Thr Pro Asp Ile Ser His
            100                 105                 110 ttc tac gtt ggc ggg tat gga agg agt gat atg cca acc ata agc cac      384
Phe Tyr Val Gly Gly Tyr Gly Arg Ser Asp Met Pro Thr Ile Ser His
        115                 120                 125 gtg acg gtg aat aat gtt ctt ctt tac aac cgt cag ctg aat gcc gag      432
Val Thr Val Asn Asn Val Leu Leu Tyr Asn Arg Gln Leu Asn Ala Glu
130                 135                 140 gag atc agg acc ttg ttc ttg agc cag gac ctg att ggc acg gaa gca      480
Glu Ile Arg Thr Leu Phe Leu Ser Gln Asp Leu Ile Gly Thr Glu Ala
145                 150                 155                 160 cac atg ggc agc agc agc ggc agc agt gcc cac ggt acg ccc tcg att      528
His Met Gly Ser Ser Ser Gly Ser Ser Ala His Gly Thr Pro Ser Ile
                165                 170                 175 ccc gtt gac agc agt gcc cac ggt aca ccc tcg act ccc gtt gac agc      576
Pro Val Asp Ser Ser Ala His Gly Thr Pro Ser Thr Pro Val Asp Ser
            180                 185                 190 agt gcc cac ggt acg ccc tcg act ccc gtt gac agc agt gcc cac ggt      624
Ser Ala His Gly Thr Pro Ser Thr Pro Val Asp Ser Ser Ala His Gly
        195                 200                 205 aca ccc tcg act ccc gtt gac agc agt gcc cac ggt aca ccc tcg act      672
Thr Pro Ser Thr Pro Val Asp Ser Ser Ala His Gly Thr Pro Ser Thr
210                 215                 220 ccc gtt gac agc agt gcc cac ggt aag ccc tcg act ccc gct gac agc      720
Pro Val Asp Ser Ser Ala His Gly Lys Pro Ser Thr Pro Ala Asp Ser
225                 230                 235                 240 agt gcc cac agt acg ccc tcg act ccc gct gac agc agt gcc cac agt      768
Ser Ala His Ser Thr Pro Ser Thr Pro Ala Asp Ser Ser Ala His Ser
                245                 250                 255 acg ccc tca att ccc gct gac agc agt gcc cac agt acg ccc tca gct      816
Thr Pro Ser Ile Pro Ala Asp Ser Ser Ala His Ser Thr Pro Ser Ala
            260                 265                 270 ccc gct gac aac ggc gcc aat ggt acg gtt ttg att ttg tcg              858
Pro Ala Asp Asn Gly Ala Asn Gly Thr Val Leu Ile Leu Ser
        275                 280                 285

<210> SEQ ID NO 44
<211> LENGTH: 286
<212> TYPE: PRT
<213> ORGANISM: Trypanosoma cruzi

<400> SEQUENCE: 44

Asp Pro Thr Tyr Arg Phe Ala Asn His Ala Phe Thr Leu Val Ala Ser
```

```
                1               5               10              15
            Val Thr Ile His Glu Val Pro Ser Val Ala Ser Pro Leu Leu Gly Ala
                            20              25              30

Ser Leu Asp Ser Ser Gly Gly Lys Lys Leu Leu Gly Leu Ser Tyr Asp
                        35              40              45

Glu Lys His Gln Trp Gln Pro Ile Tyr Gly Ser Thr Pro Val Thr Pro
                    50              55              60

Thr Gly Ser Trp Glu Met Gly Lys Arg Tyr His Val Val Leu Thr Met
                65              70              75              80

Ala Asn Lys Ile Gly Ser Val Tyr Ile Asp Gly Glu Pro Leu Glu Gly
                            85              90              95

Ser Gly Gln Thr Val Val Pro Asp Glu Arg Thr Pro Asp Ile Ser His
                        100             105             110

Phe Tyr Val Gly Gly Tyr Gly Arg Ser Asp Met Pro Thr Ile Ser His
                    115             120             125

Val Thr Val Asn Asn Val Leu Leu Tyr Asn Arg Gln Leu Asn Ala Glu
                130             135             140

Glu Ile Arg Thr Leu Phe Leu Ser Gln Asp Leu Ile Gly Thr Glu Ala
            145             150             155             160

His Met Gly Ser Ser Gly Ser Ser Ala His Gly Thr Pro Ser Ile
                        165             170             175

Pro Val Asp Ser Ser Ala His Gly Thr Pro Ser Thr Pro Val Asp Ser
                        180             185             190

Ser Ala His Gly Thr Pro Ser Thr Pro Val Asp Ser Ser Ala His Gly
                        195             200             205

Thr Pro Ser Thr Pro Val Asp Ser Ser Ala His Gly Thr Pro Ser Thr
                    210             215             220

Pro Val Asp Ser Ser Ala His Gly Lys Pro Ser Thr Pro Ala Asp Ser
            225             230             235             240

Ser Ala His Ser Thr Pro Ser Thr Pro Ala Asp Ser Ser Ala His Ser
                        245             250             255

Thr Pro Ser Ile Pro Ala Asp Ser Ser Ala His Ser Thr Pro Ser Ala
                        260             265             270

Pro Ala Asp Asn Gly Ala Asn Gly Thr Val Leu Ile Leu Ser
                    275             280             285

<210> SEQ ID NO 45
<211> LENGTH: 701
<212> TYPE: DNA
<213> ORGANISM: Trypanosoma cruzi
<220> FEATURE:
<221> NAME/KEY: CDS
<222> LOCATION: (1)..(699)

<400> SEQUENCE: 45 act cat gac gcg tac agg ccc gtt gat ccc tcg gcg tac aag cgc gcc     48
Thr His Asp Ala Tyr Arg Pro Val Asp Pro Ser Ala Tyr Lys Arg Ala
  1               5                   10                  15 ttg ccg cag gaa gag caa gag gat gtg ggg ccg cgc cac gtt gat ccc     96
Leu Pro Gln Glu Glu Gln Glu Asp Val Gly Pro Arg His Val Asp Pro
              20                  25                  30 gac cac ttc cgc tcg acc tcg acg act cat gac gcg tac agg ccc gtt    144
Asp His Phe Arg Ser Thr Ser Thr Thr His Asp Ala Tyr Arg Pro Val
          35                  40                  45 gat ccc tcg gcg tac aag cgc gcc ttg ccg cag gaa gag caa gag gat    192
Asp Pro Ser Ala Tyr Lys Arg Ala Leu Pro Gln Glu Glu Gln Glu Asp
      50                  55                  60
```

```
gtg ggg ccg cgc cac gtt gat ccc gac cac ttc cgc tcg acg act cat        240
Val Gly Pro Arg His Val Asp Pro Asp His Phe Arg Ser Thr Thr His
 65                  70                  75                  80 gac gcg tac agg ccc gtt gat ccc tcg gcg tac aag cgc gcc ttg ccg        288
Asp Ala Tyr Arg Pro Val Asp Pro Ser Ala Tyr Lys Arg Ala Leu Pro
                 85                  90                  95 cag gaa gag caa gag gat gtg ggg ccg cgc cac gtt gat ccc gac cac        336
Gln Glu Glu Gln Glu Asp Val Gly Pro Arg His Val Asp Pro Asp His
            100                 105                 110 ttc cgc tcg acc tcg acg act cat gac gcg tac agg ccc gtt gat ccc        384
Phe Arg Ser Thr Ser Thr Thr His Asp Ala Tyr Arg Pro Val Asp Pro
        115                 120                 125 tcg gcg tac aag cgc gcc ttg ccg cag gaa gag caa gag gat gtg ggg        432
Ser Ala Tyr Lys Arg Ala Leu Pro Gln Glu Glu Gln Glu Asp Val Gly
    130                 135                 140 ccg cgc cac gtt gat ccc gac cac ttc cgc tcg acc tcg acg act cat        480
Pro Arg His Val Asp Pro Asp His Phe Arg Ser Thr Ser Thr Thr His
145                 150                 155                 160 gac gcg tac agg ccc gtt gat ccc tcg gcg tac aag cgc gcc ttg ccg        528
Asp Ala Tyr Arg Pro Val Asp Pro Ser Ala Tyr Lys Arg Ala Leu Pro
                165                 170                 175 cag gaa gag caa gag gat gtg ggg ccg cgc cac gtt gat ccc gac cac        576
Gln Glu Glu Gln Glu Asp Val Gly Pro Arg His Val Asp Pro Asp His
            180                 185                 190 ttc cgc tcg acg act cat gac gcg tac agg ccc gtt gat ccc tcg gcg        624
Phe Arg Ser Thr Thr His Asp Ala Tyr Arg Pro Val Asp Pro Ser Ala
        195                 200                 205 tac aag cgc gcc ttg ccg cag gaa gag caa gag gat gtg ggg ccg cgc        672
Tyr Lys Arg Ala Leu Pro Gln Glu Glu Gln Glu Asp Val Gly Pro Arg
    210                 215                 220 cac gtt gat ccc gac cac ttc cgc tcg ac                                 701
His Val Asp Pro Asp His Phe Arg Ser
225                 230
```

<210> SEQ ID NO 46
<211> LENGTH: 233
<212> TYPE: PRT
<213> ORGANISM: Trypanosoma cruzi

<400> SEQUENCE: 46

```
Thr His Asp Ala Tyr Arg Pro Val Asp Pro Ser Ala Tyr Lys Arg Ala
 1               5                  10                  15

Leu Pro Gln Glu Glu Gln Glu Asp Val Gly Pro Arg His Val Asp Pro
            20                  25                  30

Asp His Phe Arg Ser Thr Ser Thr Thr His Asp Ala Tyr Arg Pro Val
        35                  40                  45

Asp Pro Ser Ala Tyr Lys Arg Ala Leu Pro Gln Glu Glu Gln Glu Asp
    50                  55                  60

Val Gly Pro Arg His Val Asp Pro Asp His Phe Arg Ser Thr Thr His
 65                  70                  75                  80

Asp Ala Tyr Arg Pro Val Asp Pro Ser Ala Tyr Lys Arg Ala Leu Pro
                 85                  90                  95

Gln Glu Glu Gln Glu Asp Val Gly Pro Arg His Val Asp Pro Asp His
            100                 105                 110

Phe Arg Ser Thr Ser Thr Thr His Asp Ala Tyr Arg Pro Val Asp Pro
        115                 120                 125

Ser Ala Tyr Lys Arg Ala Leu Pro Gln Glu Glu Gln Glu Asp Val Gly
    130                 135                 140

Pro Arg His Val Asp Pro Asp His Phe Arg Ser Thr Ser Thr Thr His
```

```
                145                 150                 155                 160
Asp Ala Tyr Arg Pro Val Asp Pro Ser Ala Tyr Lys Arg Ala Leu Pro
                    165                 170                 175
Gln Glu Glu Gln Glu Asp Val Gly Pro Arg His Val Asp Pro Asp His
                180                 185                 190
Phe Arg Ser Thr Thr His Asp Ala Tyr Arg Pro Val Asp Pro Ser Ala
            195                 200                 205
Tyr Lys Arg Ala Leu Pro Gln Glu Glu Gln Glu Asp Val Gly Pro Arg
        210                 215                 220
His Val Asp Pro Asp His Phe Arg Ser
225                 230

<210> SEQ ID NO 47
<211> LENGTH: 1557
<212> TYPE: DNA
<213> ORGANISM: Trypanosoma cruzi
<220> FEATURE:
<221> NAME/KEY: CDS
<222> LOCATION: (1)..(1557)

<400> SEQUENCE: 47 gat cca acg tat cgt ttt gca aac cac gcg ttc acg ctg gtg gcg tcg      48
Asp Pro Thr Tyr Arg Phe Ala Asn His Ala Phe Thr Leu Val Ala Ser
 1               5                  10                  15 gtg acg att cac gag gtt ccg agc gtc gcg agt cct ttg ctg ggt gcg      96
Val Thr Ile His Glu Val Pro Ser Val Ala Ser Pro Leu Leu Gly Ala
             20                  25                  30 agc ctg gac tct tct ggt ggc aaa aaa ctc ctg ggg ctc tcg tac gac     144
Ser Leu Asp Ser Ser Gly Gly Lys Lys Leu Leu Gly Leu Ser Tyr Asp
         35                  40                  45 gag aag cac cag tgg cag cca ata tac gga tca acg ccg gtg acg ccg     192
Glu Lys His Gln Trp Gln Pro Ile Tyr Gly Ser Thr Pro Val Thr Pro
     50                  55                  60 acc gga tcg tgg gag atg ggt aag agg tac cac gtg gtt ctt acg atg     240
Thr Gly Ser Trp Glu Met Gly Lys Arg Tyr His Val Val Leu Thr Met
 65                  70                  75                  80 gcg aat aaa att ggc tcc gtg tac att gat gga gaa cct ctg gag ggt     288
Ala Asn Lys Ile Gly Ser Val Tyr Ile Asp Gly Glu Pro Leu Glu Gly
                 85                  90                  95 tca ggg cag acc gtt gtg cca gac gag agg acg cct gac atc tcc cac     336
Ser Gly Gln Thr Val Val Pro Asp Glu Arg Thr Pro Asp Ile Ser His
            100                 105                 110 ttc tac gtt ggc ggg tat gga agg agt gat atg cca acc ata agc cac     384
Phe Tyr Val Gly Gly Tyr Gly Arg Ser Asp Met Pro Thr Ile Ser His
        115                 120                 125 gtg acg gtg aat aat gtt ctt ctt tac aac cgt cag ctg aat gcc gag     432
Val Thr Val Asn Asn Val Leu Leu Tyr Asn Arg Gln Leu Asn Ala Glu
    130                 135                 140 gag atc agg acc ttg ttc ttg agc cag gac ctg att ggc acg gaa gca     480
Glu Ile Arg Thr Leu Phe Leu Ser Gln Asp Leu Ile Gly Thr Glu Ala
145                 150                 155                 160 cac atg ggc agc agc agc ggc agc agt gcc cac ggt acg ccc tcg att     528
His Met Gly Ser Ser Ser Gly Ser Ser Ala His Gly Thr Pro Ser Ile
                165                 170                 175 ccc gtt gac agc agt gcc cac ggt aca ccc tcg act ccc gtt gac agc     576
Pro Val Asp Ser Ser Ala His Gly Thr Pro Ser Thr Pro Val Asp Ser
            180                 185                 190 agt gcc cac ggt acg ccc tcg act ccc gtt gac agc agt gcc cac ggt     624
Ser Ala His Gly Thr Pro Ser Thr Pro Val Asp Ser Ser Ala His Gly
        195                 200                 205
```

```
aca ccc tcg act ccc gtt gac agc agt gcc cac ggt aca ccc tcg act       672
Thr Pro Ser Thr Pro Val Asp Ser Ser Ala His Gly Thr Pro Ser Thr
    210                 215                 220 ccc gtt gac agc agt gcc cac ggt aag ccc tcg act ccc gct gac agc       720
Pro Val Asp Ser Ser Ala His Gly Lys Pro Ser Thr Pro Ala Asp Ser
225                 230                 235                 240 agt gcc cac agt acg ccc tcg act ccc gct gac agc agt gcc cac agt       768
Ser Ala His Ser Thr Pro Ser Thr Pro Ala Asp Ser Ser Ala His Ser
                245                 250                 255 acg ccc tca att ccc gct gac agc agt gcc cac agt acg ccc tca gct       816
Thr Pro Ser Ile Pro Ala Asp Ser Ser Ala His Ser Thr Pro Ser Ala
            260                 265                 270 ccc gct gac aac ggc gcc aat ggt acg gtt ttg att ttg tcg act cat       864
Pro Ala Asp Asn Gly Ala Asn Gly Thr Val Leu Ile Leu Ser Thr His
        275                 280                 285 gac gcg tac agg ccc gtt gat ccc tcg gcg tac aag cgc gcc ttg ccg       912
Asp Ala Tyr Arg Pro Val Asp Pro Ser Ala Tyr Lys Arg Ala Leu Pro
    290                 295                 300 cag gaa gag caa gag gat gtg ggg ccg cgc cac gtt gat ccc gac cac       960
Gln Glu Glu Gln Glu Asp Val Gly Pro Arg His Val Asp Pro Asp His
305                 310                 315                 320 ttc cgc tcg acc tcg acg act cat gac gcg tac agg ccc gtt gat ccc      1008
Phe Arg Ser Thr Ser Thr Thr His Asp Ala Tyr Arg Pro Val Asp Pro
                325                 330                 335 tcg gcg tac aag cgc gcc ttg ccg cag gaa gag caa gag gat gtg ggg      1056
Ser Ala Tyr Lys Arg Ala Leu Pro Gln Glu Glu Gln Glu Asp Val Gly
            340                 345                 350 ccg cgc cac gtt gat ccc gac cac ttc cgc tcg acg act cat gac gcg      1104
Pro Arg His Val Asp Pro Asp His Phe Arg Ser Thr Thr His Asp Ala
        355                 360                 365 tac agg ccc gtt gat ccc tcg gcg tac aag cgc gcc ttg ccg cag gaa      1152
Tyr Arg Pro Val Asp Pro Ser Ala Tyr Lys Arg Ala Leu Pro Gln Glu
    370                 375                 380 gag caa gag gat gtg ggg ccg cgc cac gtt gat ccc gac cac ttc cgc      1200
Glu Gln Glu Asp Val Gly Pro Arg His Val Asp Pro Asp His Phe Arg
385                 390                 395                 400 tcg acc tcg acg act cat gac gcg tac agg ccc gtt gat ccc tcg gcg      1248
Ser Thr Ser Thr Thr His Asp Ala Tyr Arg Pro Val Asp Pro Ser Ala
                405                 410                 415 tac aag cgc gcc ttg ccg cag gaa gag caa gag gat gtg ggg ccg cgc      1296
Tyr Lys Arg Ala Leu Pro Gln Glu Glu Gln Glu Asp Val Gly Pro Arg
            420                 425                 430 cac gtt gat ccc gac cac ttc cgc tcg acc tcg acg act cat gac gcg      1344
His Val Asp Pro Asp His Phe Arg Ser Thr Ser Thr Thr His Asp Ala
        435                 440                 445 tac agg ccc gtt gat ccc tcg gcg tac aag cgc gcc ttg ccg cag gaa      1392
Tyr Arg Pro Val Asp Pro Ser Ala Tyr Lys Arg Ala Leu Pro Gln Glu
    450                 455                 460 gag caa gag gat gtg ggg ccg cgc cac gtt gat ccc gac cac ttc cgc      1440
Glu Gln Glu Asp Val Gly Pro Arg His Val Asp Pro Asp His Phe Arg
465                 470                 475                 480 tcg acg act cat gac gcg tac agg ccc gtt gat ccc tcg gcg tac aag      1488
Ser Thr Thr His Asp Ala Tyr Arg Pro Val Asp Pro Ser Ala Tyr Lys
                485                 490                 495 cgc gcc ttg ccg cag gaa gag caa gag gat gtg ggg ccg cgc cac gtt      1536
Arg Ala Leu Pro Gln Glu Glu Gln Glu Asp Val Gly Pro Arg His Val
            500                 505                 510 gat ccc gac cac ttc cgc tcg                                          1557
Asp Pro Asp His Phe Arg Ser
            515
```

```
<210> SEQ ID NO 48
<211> LENGTH: 519
<212> TYPE: PRT
<213> ORGANISM: Trypanosoma cruzi

<400> SEQUENCE: 48

Asp Pro Thr Tyr Arg Phe Ala Asn His Ala Phe Thr Leu Val Ala Ser
  1               5                  10                  15

Val Thr Ile His Glu Val Pro Ser Val Ala Ser Pro Leu Leu Gly Ala
                 20                  25                  30

Ser Leu Asp Ser Ser Gly Gly Lys Lys Leu Leu Gly Leu Ser Tyr Asp
             35                  40                  45

Glu Lys His Gln Trp Gln Pro Ile Tyr Gly Ser Thr Pro Val Thr Pro
         50                  55                  60

Thr Gly Ser Trp Glu Met Gly Lys Arg Tyr His Val Val Leu Thr Met
 65                  70                  75                  80

Ala Asn Lys Ile Gly Ser Val Tyr Ile Asp Gly Glu Pro Leu Glu Gly
                 85                  90                  95

Ser Gly Gln Thr Val Val Pro Asp Glu Arg Thr Pro Asp Ile Ser His
            100                 105                 110

Phe Tyr Val Gly Gly Tyr Gly Arg Ser Asp Met Pro Thr Ile Ser His
            115                 120                 125

Val Thr Val Asn Asn Val Leu Leu Tyr Asn Arg Gln Leu Asn Ala Glu
        130                 135                 140

Glu Ile Arg Thr Leu Phe Leu Ser Gln Asp Leu Ile Gly Thr Glu Ala
145                 150                 155                 160

His Met Gly Ser Ser Gly Ser Ser Ala His Gly Thr Pro Ser Ile
                165                 170                 175

Pro Val Asp Ser Ser Ala His Gly Thr Pro Ser Thr Pro Val Asp Ser
            180                 185                 190

Ser Ala His Gly Thr Pro Ser Thr Pro Val Asp Ser Ser Ala His Gly
        195                 200                 205

Thr Pro Ser Thr Pro Val Asp Ser Ser Ala His Gly Thr Pro Ser Thr
210                 215                 220

Pro Val Asp Ser Ser Ala His Gly Lys Pro Ser Thr Pro Ala Asp Ser
225                 230                 235                 240

Ser Ala His Ser Thr Pro Ser Thr Pro Ala Asp Ser Ser Ala His Ser
                245                 250                 255

Thr Pro Ser Ile Pro Ala Asp Ser Ser Ala His Ser Thr Pro Ser Ala
            260                 265                 270

Pro Ala Asp Asn Gly Ala Asn Gly Thr Val Leu Ile Leu Ser Thr His
        275                 280                 285

Asp Ala Tyr Arg Pro Val Asp Pro Ser Ala Tyr Lys Arg Ala Leu Pro
        290                 295                 300

Gln Glu Glu Gln Glu Asp Val Gly Pro Arg His Val Asp Pro Asp His
305                 310                 315                 320

Phe Arg Ser Thr Ser Thr Thr His Asp Ala Tyr Arg Pro Val Asp Pro
                325                 330                 335

Ser Ala Tyr Lys Arg Ala Leu Pro Gln Glu Glu Gln Glu Asp Val Gly
            340                 345                 350

Pro Arg His Val Asp Pro Asp His Phe Arg Ser Thr Thr His Asp Ala
        355                 360                 365

Tyr Arg Pro Val Asp Pro Ser Ala Tyr Lys Arg Ala Leu Pro Gln Glu
    370                 375                 380
```

```
Glu Gln Glu Asp Val Gly Pro Arg His Val Asp Pro Asp His Phe Arg
385                 390                 395                 400

Ser Thr Ser Thr Thr His Asp Ala Tyr Arg Pro Val Asp Pro Ser Ala
                405                 410                 415

Tyr Lys Arg Ala Leu Pro Gln Glu Glu Gln Glu Asp Val Gly Pro Arg
            420                 425                 430

His Val Asp Pro Asp His Phe Arg Ser Thr Ser Thr Thr His Asp Ala
        435                 440                 445

Tyr Arg Pro Val Asp Pro Ser Ala Tyr Lys Arg Ala Leu Pro Gln Glu
    450                 455                 460

Glu Gln Glu Asp Val Gly Pro Arg His Val Asp Pro Asp His Phe Arg
465                 470                 475                 480

Ser Thr Thr His Asp Ala Tyr Arg Pro Val Asp Pro Ser Ala Tyr Lys
                485                 490                 495

Arg Ala Leu Pro Gln Glu Gln Glu Asp Val Gly Pro Arg His Val
            500                 505                 510

Asp Pro Asp His Phe Arg Ser
            515

<210> SEQ ID NO 49
<211> LENGTH: 1521
<212> TYPE: DNA
<213> ORGANISM: Trypanosoma cruzi
<220> FEATURE:
<221> NAME/KEY: CDS
<222> LOCATION: (1)..(1521)

<400> SEQUENCE: 49 atg gcc cga gct gtg gtg ctt gag gat gga gcg ctt tac gtg gcg gac      48
Met Ala Arg Ala Val Val Leu Glu Asp Gly Ala Leu Tyr Val Ala Asp
1               5                   10                  15 aat gcc aac aac ctc gtt cga gaa atc tcc aat ggc gtt gtc act tcg      96
Asn Ala Asn Asn Leu Val Arg Glu Ile Ser Asn Gly Val Val Thr Ser
            20                  25                  30 ttt att acg gaa gga ctg ctg ggc cca tcg tac atc aaa ccg tac agc      144
Phe Ile Thr Glu Gly Leu Leu Gly Pro Ser Tyr Ile Lys Pro Tyr Ser
        35                  40                  45 cgt aca aat ggc gct cat gac ttg ttt gtg tcg gac acg ggc aaa tca      192
Arg Thr Asn Gly Ala His Asp Leu Phe Val Ser Asp Thr Gly Lys Ser
    50                  55                  60 cgc atc att ttt gcc cca cct cag aaa aaa acg ttc atc aca gtg ttt      240
Arg Ile Ile Phe Ala Pro Pro Gln Lys Lys Thr Phe Ile Thr Val Phe
65                  70                  75                  80 ata aca gga ttc cag ccg gat gtt ctt caa att agc gag aag agt cgt      288
Ile Thr Gly Phe Gln Pro Asp Val Leu Gln Ile Ser Glu Lys Ser Arg
                85                  90                  95 ttg atg ttt gcc atc tgc aat tcc acg aaa att ctt gcg att aat atg      336
Leu Met Phe Ala Ile Cys Asn Ser Thr Lys Ile Leu Ala Ile Asn Met
            100                 105                 110 cag gga gcc aca acc ccg aag gag tac tgg caa gtt gga aat gcg gac      384
Gln Gly Ala Thr Thr Pro Lys Glu Tyr Trp Gln Val Gly Asn Ala Asp
        115                 120                 125 tgc atg ggc tat cag agt tcc ctc atg ctc acg acc gag gag gat aaa      432
Cys Met Gly Tyr Gln Ser Ser Leu Met Leu Thr Thr Glu Glu Asp Lys
    130                 135                 140 ctc ctc tac tac ggc ata tta aat gga acc cca tcc atc atg tct tta      480
Leu Leu Tyr Tyr Gly Ile Leu Asn Gly Thr Pro Ser Ile Met Ser Leu
145                 150                 155                 160 ccc gcc acc aaa acg aag acg gaa gca ccc aga att tgc ccg gat gtg      528
Pro Ala Thr Lys Thr Lys Thr Glu Ala Pro Arg Ile Cys Pro Asp Val
```

```
                          165                 170                 175
ttg ttg cag tgg cca cat ggg ccc att gtt tcg ctt gtg aat att aac     576
Leu Leu Gln Trp Pro His Gly Pro Ile Val Ser Leu Val Asn Ile Asn
                180                 185                 190 aaa cat gca ttt tac gtt gtt acc gcc tcc aat gta tac att gta cat     624
Lys His Ala Phe Tyr Val Val Thr Ala Ser Asn Val Tyr Ile Val His
            195                 200                 205 gat ggc tcg tat cat ccg act gga tcc atg gcc cag ctc caa cag gca     672
Asp Gly Ser Tyr His Pro Thr Gly Ser Met Ala Gln Leu Gln Gln Ala
        210                 215                 220 gaa aat aat atc act aat tcc aaa aaa gaa atg aca aag cta cga gaa     720
Glu Asn Asn Ile Thr Asn Ser Lys Lys Glu Met Thr Lys Leu Arg Glu
225                 230                 235                 240 aaa gtg aaa aag gcc gag aaa gaa aaa ttg gac gcc att aac cgg gca     768
Lys Val Lys Lys Ala Glu Lys Glu Lys Leu Asp Ala Ile Asn Arg Ala
                245                 250                 255 acc aag ctg gaa gag gaa cga aac caa gcg tac aaa gca gca cac aag     816
Thr Lys Leu Glu Glu Glu Arg Asn Gln Ala Tyr Lys Ala Ala His Lys
            260                 265                 270 gca gag gag gaa aag gct aaa aca ttt caa cgc ctt ata aca ttt gag     864
Ala Glu Glu Glu Lys Ala Lys Thr Phe Gln Arg Leu Ile Thr Phe Glu
        275                 280                 285 tcg gaa aat att aac tta aag aaa agg cca aat gac gca gtt tca aat     912
Ser Glu Asn Ile Asn Leu Lys Lys Arg Pro Asn Asp Ala Val Ser Asn
290                 295                 300 cgg gat aag aaa aaa aat tct gaa acc gca aaa act gac gaa gta gag     960
Arg Asp Lys Lys Lys Asn Ser Glu Thr Ala Lys Thr Asp Glu Val Glu
305                 310                 315                 320 aaa cag agg gcg gct gag gct gcc aag gcc gtg gag acg gag aag cag    1008
Lys Gln Arg Ala Ala Glu Ala Ala Lys Ala Val Glu Thr Glu Lys Gln
                325                 330                 335 agg gca gct gag gcc acg aag gtt gcc gaa gcg gag aag cgg aag gca    1056
Arg Ala Ala Glu Ala Thr Lys Val Ala Glu Ala Glu Lys Arg Lys Ala
            340                 345                 350 gct gag gcc gcc aag gcc gtg gag acg gag aag cag agg gca gct gaa    1104
Ala Glu Ala Ala Lys Ala Val Glu Thr Glu Lys Gln Arg Ala Ala Glu
        355                 360                 365 gcc acg aag gtt gcc gaa gcg gag aag cag aag gca gct gag gcc gcc    1152
Ala Thr Lys Val Ala Glu Ala Glu Lys Gln Lys Ala Ala Glu Ala Ala
370                 375                 380 aag gcc gtg gag acg gag aag cag agg gca gct gaa gcc acg aag gtt    1200
Lys Ala Val Glu Thr Glu Lys Gln Arg Ala Ala Glu Ala Thr Lys Val
385                 390                 395                 400 gcc gaa gcg gag aag cag agg gca gct gaa gcc atg aag gtt gcc gaa    1248
Ala Glu Ala Glu Lys Gln Arg Ala Ala Glu Ala Met Lys Val Ala Glu
                405                 410                 415 gcg gag aag cag aag gca gct gag gcc gcc aag gcc gtg gag acg gag    1296
Ala Glu Lys Gln Lys Ala Ala Glu Ala Ala Lys Ala Val Glu Thr Glu
            420                 425                 430 aag cag agg gca gct gaa gcc acg aag gtt gcc gaa gcg gag aag cag    1344
Lys Gln Arg Ala Ala Glu Ala Thr Lys Val Ala Glu Ala Glu Lys Gln
        435                 440                 445 aag gca gct gag gcc gcc aag gcc gtg gag acg gag aag cag agg gca    1392
Lys Ala Ala Glu Ala Ala Lys Ala Val Glu Thr Glu Lys Gln Arg Ala
450                 455                 460 gct gaa gcc acg aag gtt gcc gaa gcg gag aag cag aag gca gct gag    1440
Ala Glu Ala Thr Lys Val Ala Glu Ala Glu Lys Gln Lys Ala Ala Glu
465                 470                 475                 480 gcc gcc aag gcc gtg gag acg gag aag cag agg gca gct gaa gcc acg    1488
Ala Ala Lys Ala Val Glu Thr Glu Lys Gln Arg Ala Ala Glu Ala Thr
```

```
                    485                 490                 495
aag gtt gcc gaa gcg gag aag gat atc gat ccc                              1521
Lys Val Ala Glu Ala Glu Lys Asp Ile Asp Pro
        500                 505

<210> SEQ ID NO 50
<211> LENGTH: 507
<212> TYPE: PRT
<213> ORGANISM: Trypanosoma cruzi

<400> SEQUENCE: 50

Met Ala Arg Ala Val Val Leu Glu Asp Gly Ala Leu Tyr Val Ala Asp
  1               5                  10                  15

Asn Ala Asn Asn Leu Val Arg Glu Ile Ser Asn Gly Val Val Thr Ser
             20                  25                  30

Phe Ile Thr Glu Gly Leu Leu Gly Pro Ser Tyr Ile Lys Pro Tyr Ser
         35                  40                  45

Arg Thr Asn Gly Ala His Asp Leu Phe Val Ser Asp Thr Gly Lys Ser
     50                  55                  60

Arg Ile Ile Phe Ala Pro Pro Gln Lys Lys Thr Phe Ile Thr Val Phe
 65                  70                  75                  80

Ile Thr Gly Phe Gln Pro Asp Val Leu Gln Ile Ser Glu Lys Ser Arg
                 85                  90                  95

Leu Met Phe Ala Ile Cys Asn Ser Thr Lys Ile Leu Ala Ile Asn Met
            100                 105                 110

Gln Gly Ala Thr Thr Pro Lys Glu Tyr Trp Gln Val Gly Asn Ala Asp
        115                 120                 125

Cys Met Gly Tyr Gln Ser Ser Leu Met Leu Thr Thr Glu Glu Asp Lys
    130                 135                 140

Leu Leu Tyr Tyr Gly Ile Leu Asn Gly Thr Pro Ser Ile Met Ser Leu
145                 150                 155                 160

Pro Ala Thr Lys Thr Lys Thr Glu Ala Pro Arg Ile Cys Pro Asp Val
                165                 170                 175

Leu Leu Gln Trp Pro His Gly Pro Ile Val Ser Leu Val Asn Ile Asn
            180                 185                 190

Lys His Ala Phe Tyr Val Val Thr Ala Ser Asn Val Tyr Ile Val His
        195                 200                 205

Asp Gly Ser Tyr His Pro Thr Gly Ser Met Ala Gln Leu Gln Gln Ala
    210                 215                 220

Glu Asn Asn Ile Thr Asn Ser Lys Lys Glu Met Thr Lys Leu Arg Glu
225                 230                 235                 240

Lys Val Lys Lys Ala Glu Lys Glu Lys Leu Asp Ala Ile Asn Arg Ala
                245                 250                 255

Thr Lys Leu Glu Glu Glu Arg Asn Gln Ala Tyr Lys Ala Ala His Lys
            260                 265                 270

Ala Glu Glu Glu Lys Ala Lys Thr Phe Gln Arg Leu Ile Thr Phe Glu
        275                 280                 285

Ser Glu Asn Ile Asn Leu Lys Lys Arg Pro Asn Asp Ala Val Ser Asn
    290                 295                 300

Arg Asp Lys Lys Lys Asn Ser Glu Thr Ala Lys Thr Asp Glu Val Glu
305                 310                 315                 320

Lys Gln Arg Ala Ala Glu Ala Lys Ala Val Glu Thr Glu Lys Gln
                325                 330                 335

Arg Ala Ala Glu Ala Thr Lys Val Ala Glu Ala Glu Lys Arg Lys Ala
            340                 345                 350
```

-continued

```
Ala Glu Ala Ala Lys Ala Val Glu Thr Glu Lys Gln Arg Ala Ala Glu
        355                 360                 365

Ala Thr Lys Val Ala Glu Ala Glu Lys Gln Lys Ala Ala Glu Ala Ala
    370                 375                 380

Lys Ala Val Glu Thr Glu Lys Gln Arg Ala Ala Glu Ala Thr Lys Val
385                 390                 395                 400

Ala Glu Ala Glu Lys Gln Arg Ala Ala Glu Ala Met Lys Val Ala Glu
                405                 410                 415

Ala Glu Lys Gln Lys Ala Ala Glu Ala Lys Ala Val Glu Thr Glu
            420                 425                 430

Lys Gln Arg Ala Ala Glu Ala Thr Lys Val Ala Glu Ala Glu Lys Gln
                435                 440                 445

Lys Ala Ala Glu Ala Ala Lys Ala Val Glu Thr Glu Lys Gln Arg Ala
        450                 455                 460

Ala Glu Ala Thr Lys Val Ala Glu Ala Glu Lys Gln Lys Ala Ala Glu
465                 470                 475                 480

Ala Ala Lys Ala Val Glu Thr Glu Lys Gln Arg Ala Ala Glu Ala Thr
                485                 490                 495

Lys Val Ala Glu Ala Glu Lys Asp Ile Asp Pro
            500                 505

<210> SEQ ID NO 51
<211> LENGTH: 34
<212> TYPE: PRT
<213> ORGANISM: Trypanosoma cruzi

<400> SEQUENCE: 51

Ser Thr Asp Lys Leu Lys Leu Asn Gln Gln Asn Lys Pro His Ile Ala
1               5                   10                  15

Asn Asn Lys Gln Lys Thr Thr Leu Glu Lys Thr Gln Thr Glu Gln Lys
            20                  25                  30

Thr Ala

<210> SEQ ID NO 52
<211> LENGTH: 12
<212> TYPE: PRT
<213> ORGANISM: Trypanosoma cruzi

<400> SEQUENCE: 52

Pro Phe Gly Gln Ala Ala Ala Gly Asp Lys Pro Ser
1               5                   10

<210> SEQ ID NO 53
<211> LENGTH: 21
<212> TYPE: PRT
<213> ORGANISM: Trypanosoma cruzi

<400> SEQUENCE: 53

Gly Thr Ala Phe Asp Ala Ser Arg Ser Thr Val Phe Ala Asn Ala Pro
1               5                   10                  15

Gly Val Ala Gln Val
            20

<210> SEQ ID NO 54
<211> LENGTH: 68
<212> TYPE: PRT
<213> ORGANISM: Trypanosoma cruzi

<400> SEQUENCE: 54

Met Glu Gln Glu Arg Arg Gln Leu Leu Glu Lys Asp Pro Arg Arg Asn
```

```
                1               5                  10                  15
Ala Lys Glu Ile Ala Ala Leu Glu Glu Ser Met Asn Ala Arg Ala Gln
                        20                  25                  30

Glu Leu Ala Arg Glu Lys Lys Leu Ala Asp Arg Ala Phe Leu Asp Gln
                35                  40                  45

Lys Pro Glu Gly Val Pro Leu Arg Glu Leu Pro Leu Asp Asp Asp Ser
        50                  55                  60

Asp Phe Val Ala
65

<210> SEQ ID NO 55
<211> LENGTH: 85
<212> TYPE: PRT
<213> ORGANISM: Trypanosoma cruzi

<400> SEQUENCE: 55

Met Ala Gln Leu Gln Gln Ala Glu Asn Asn Ile Thr Asn Ser Lys Lys
1               5                  10                  15

Glu Met Thr Lys Leu Arg Glu Lys Val Lys Ala Glu Lys Glu Lys
                20                  25                  30

Leu Asp Ala Ile Asn Arg Ala Thr Lys Leu Glu Glu Glu Arg Asn Gln
                35                  40                  45

Ala Tyr Lys Ala Ala His Lys Ala Glu Glu Lys Ala Lys Thr Phe
        50                  55                  60

Gln Arg Leu Ile Thr Phe Glu Ser Glu Asn Ile Asn Leu Lys Lys Arg
65                  70                  75                  80

Pro Asn Asp Ala Val
                85

<210> SEQ ID NO 56
<211> LENGTH: 14
<212> TYPE: PRT
<213> ORGANISM: Trypanosoma cruzi

<400> SEQUENCE: 56

Gln Arg Ala Ala Glu Ala Ala Lys Ala Val Glu Thr Glu Lys
1               5                  10

<210> SEQ ID NO 57
<211> LENGTH: 214
<212> TYPE: PRT
<213> ORGANISM: Trypanosoma cruzi

<400> SEQUENCE: 57

Asp Ile Asp Pro Met Gly Ala Cys Gly Ser Lys Asp Ser Thr Ser Asp
1               5                  10                  15

Lys Gly Leu Ala Ser Asp Lys Asp Gly Lys Asn Ala Lys Asp Arg Lys
                20                  25                  30

Glu Ala Trp Glu Arg Ile Arg Gln Ala Ile Pro Arg Glu Lys Thr Ala
                35                  40                  45

Glu Ala Lys Gln Arg Arg Ile Glu Leu Phe Lys Lys Phe Asp Lys Asn
        50                  55                  60

Glu Thr Gly Lys Leu Cys Tyr Asp Glu Val His Ser Gly Cys Leu Glu
65                  70                  75                  80

Val Leu Lys Leu Asp Glu Phe Thr Pro Arg Val Arg Asp Ile Thr Lys
                85                  90                  95

Arg Ala Phe Asp Lys Ala Arg Ala Leu Gly Ser Lys Leu Glu Asn Lys
                100                 105                 110
```

-continued

```
Gly Ser Glu Asp Phe Val Glu Phe Leu Glu Phe Arg Leu Met Leu Cys
        115                 120                 125

Tyr Ile Tyr Asp Phe Phe Glu Leu Thr Val Met Phe Asp Glu Ile Asp
        130                 135                 140

Ala Ser Gly Asn Met Leu Val Asp Glu Glu Glu Phe Lys Arg Ala Val
145                 150                 155                 160

Pro Lys Leu Glu Ala Trp Gly Ala Lys Val Glu Asp Pro Ala Ala Leu
                165                 170                 175

Phe Lys Glu Leu Asp Lys Asn Gly Thr Gly Ser Val Thr Phe Asp Glu
                180                 185                 190

Phe Ala Ala Trp Ala Ser Ala Val Lys Leu Asp Ala Asp Gly Asp Pro
        195                 200                 205

Asp Asn Val Pro Asp Ile
    210
```

RECOMBINANT POLYPEPTIDES FOR DIAGNOSING INFECTION WITH *TRYPANOSOMA CRUZI*

CROSS-REFERENCE TO RELATED APPLICATIONS

This application is a Division of prior application Ser. No. 12/355,338, filed Jan. 16, 2009, now abandoned, which in turn is a Division of Ser. No. 10/726,692, filed Dec. 4, 2003, now U.S. Pat. No. 7,491,515 which claims priority from U.S. Provisional Application No. 60/430,654, filed Dec. 4, 2002, hereby incorporated by reference in its entirety.

BACKGROUND OF THE INVENTION

1. Field of the Invention

The present invention relates to recombinant polypeptides that are useful for diagnosing American trypanosomiasis, or Chagas disease. Chagas disease is caused by the infectious agent *Trypanosoma cruzi*. More particularly, the invention relates to specific combinations of recombinant *T. cruzi* polypeptides, synthesized using genetic engineering techniques, and to constructs and processes for producing the recombinant polypeptides, and to an assay and kit for detecting *T. cruzi* infection which employs the recombinant polypeptides.

2. Background

Chagas disease is a zoonosis caused by the protozoan parasite, *Trypanosoma cruzi*. This organism is primarily transmitted through contact with its triatomine insect vectors, but transmission by transfusion of contaminated blood and congenital transmission also are important. Historically Chagas disease has been a public health problem in all of Latin America, with the exception of the Caribbean nations. The World Health Organization estimates that 16-18 million persons are chronically infected with *T. cruzi*, and that 45,000 deaths occur each year due to the illness. Infection with *T. cruzi* is life-long and specific drug treatment lacks efficacy and often causes serious side effects. Ten to thirty percent of *T. cruzi*-infected persons develop chronic symptomatic Chagas disease, and the burden of disability and mortality in the endemic countries is enormous.

An estimated 80,000 to 100,000 *T. cruzi*-infected persons now live in the United States. These immigrants pose a risk for transfusion-associated transmission of the parasite here and in other countries to which Latin Americans have emigrated. Eight such cases have been reported in the United States, Canada, and Europe, all of which occurred in immunosuppressed patients in whom acute *T. cruzi* infection was diagnosed because of the fulminant course of the illness. Most transfusions are given to immunocompetent patients in whom acute Chagas disease would be a mild illness, and thus it is reasonable to assume that many other undetected instances of transfusion-associated transmission of *T. cruzi* have occurred in the United States and other industrialized nations. The question of whether blood donated in the United States should be screened serologically for antibodies to *T. cruzi* has been considered for at least a decade by both public and private entities involved in blood banking. A panel of experts convened in early 2000 by the American Red Cross to consider this issue recommended unanimously that our blood supply be screened serologically. Implementation of such a recommendation, however, is not an option currently because no test for *T. cruzi* infection has been cleared by the FDA for screening donated blood.

Diagnosis of *T. cruzi* infection presents problems. Demographic and clinical data are suggestive at best. Parasitologic tests, e.g., xenodianosis, hemoculture and PCR are insensitive. Other serologic tests are generally insensitive and lack specificity, as false positive reactions often occur with specimens from patients having infectious diseases, such as leishmaniasis, syphilis, or malaria; autoimmune diseases; and other parasitic and non-parasitic illnesses.

Such conventional tests include indirect immunofluorescence (IIF), indirect hemagglutination (IHA), and complement fixation (CF) tests, as well as enzyme-linked immunosorbent assays (ELISA or EIA). Due to the lack of sensitivity and specify of the three commonly used assays, when a sample has a positive result from any, the blood must be discarded. Table I shows that in a major Brazilian blood bank (Hemocentro, são Paulo, Brazil), up to 3.43% of blood donations fall into this category.

TABLE I

| IIF | IHA | CF | % w/ Results |
|-----|-----|-----|--------------|
| +   | +   | +   | 0.68%        |
| +   | −   | +   | 0.71%        |
| +   | +   | −   |              |
| −   | +   | +   |              |
| +   | −   | −   | 2.04%        |
| −   | +   | −   |              |
| −   | −   | +   |              |
| TOTAL: | | | 3.43% |

Commercially available ELISAs include lysate-based tests such as the Chagas Enzyme Immunoassay (EIA), available from Abbott Laboratories of Abbott Park, Ill. (the subject of FDA 510(k) Premarket Notification No. K933716, herein incorporated by reference in its entirety); the Chagas' IgG ELISA, available from Meridian Bioscience, Inc. of Cincinnati, Ohio, and its predecessor, Gull Laboratories (the subject of FDA 510(k) Premarket Notification No. K911233, herein incorporated by reference in its entirety); and the Chagas' kit (EIA method), available from Hemagen Diagnostics, Inc., of Waltham, Mass. (the subject of FDA 510(k) Premarket Notification No. K930272, herein incorporated by reference in its entirely). However, because these tests have less than optimal sensitivities and specificities, their use for screening donated blood would fail to detect some *T. cruzi*-infected units and also would cause substantial numbers of otherwise usable units to be discarded needlessly.

One of the present inventors has previously developed a radioimmune precipitation assay (RIPA), described in Kirchhoff L V, Gam A A, Gusmao R D, Goldsmith R S, Rezende J M, Rassi A. "Increased specificity of serodiagnosis of Chagas' disease by detection of antibody to the 72 and 90 kDa glycoproteins of *Trypanosoma cruzi*." J Infect Dis 1987; 155: 561-564, herein incorporated by reference in its entirety. This test is considered the benchmark against which other tests are measured, and it is the only current option for confirmatory testing in the United States. Unfortunately, the RIPA costs $175 per assay, and at that price, screening the approximately 13 million units of blood donated each year would cost over $2 billion.

Therefore, the present inventors have further developed recombinant assays for detection of *T. cruzi* infection. A typical recombinant polypeptide and method for assaying is described by them in U.S. Pat. No. 5,876,734, No. 6,228,601, and PCT Publication No. WO 95/25797, each of which is herein incorporated by reference in its entirety. Such assays for *T. cruzi* infection based on recombinant antigens, in contrast to those utilizing native antigens (e.g., the conventional lysate-based assays), as discussed above, will be more accurate, i.e., the sensitivity and specificity will be higher.

Furthermore, the recombinant assays of the invention present manufacturing advantages over the materials for the RIPA and conventional tests. Once the molecular biology has been completed, the recombinant antigens are produced in *Escherichia coli*, thus eliminating completely any biohazard associated with growing the parasites in liquid culture. This is a substantive advantage, as many cases of laboratory-acquired *T. cruzi* infection have been reported. Additionally, recombinant antigens produced in *E. coli* are much easier to purify, quantitate, and standardize than antigen lysates produced in liquid cultures of parasites, thus facilitating the manufacture of a consistent product and simplifying compliance with governmental regulations. A final advantage lies in the fact that several of the recombinant proteins presented in this application are comprised of two to four distinct protein segments derived from separate *T. cruzi* genes. This use of hybrid recombinant proteins also facilitates manufacture of an assay in that several antigenically distinct proteins are obtained in a single purification, quantitation, and standardization run.

SUMMARY OF THE INVENTION

The present invention utilizes recombinant proteins for detecting *T. cruzi* infected blood. The invention utilizes specific polypeptide sequences that correspond to fusion proteins FP3, FP4, FP5, FP6, FP7, FP8, FP9 and FP10 as described below. Isolated polynucleotides that encode the inventive polypeptides according to the present invention are also utilized, as are cells transformed with a recombinant plasmid that expresses a polypeptide according to the invention. The present invention is similar to that which is described in U.S. Pat. No. 5,876,734, herein incorporated by reference in its entirety. However, the present invention replaces the proteins in the process with the recombinant proteins of this invention to achieve similar or superior results.

The present invention also provides a method for detecting the presence of antibodies to *T. cruzi* in an individual, comprising the steps of contacting a putative anti-*T. cruzi* antibody-containing sample from an individual with a polypeptide according to the invention that is typically attached or conjugated to a carrier molecule or attached or conjugated to a solid phase; allowing anti-*T. cruzi* and other antibodies in said sample to bind to said polypeptide; washing away unbound anti-*T. cruzi* antibodies; and adding a compound that enables detection of the anti-*T. cruzi* antibodies which are specifically bound to the polypeptide. The compound that enables detection of the anti-*T. cruzi* antibodies may be selected from the group consisting of a colorometric agent, a fluorescent agent, a chemiluminescent agent and a radionucleotide.

Also provided in accordance with the present invention is a kit for diagnosing the presence of anti-*T. cruzi* antibodies in a sample, comprising a container in which a polypeptide according to the invention is attached or conjugated to a carrier molecule or attached or conjugated to a solid phase; and directions for carrying out the method according to the invention. The kit additionally may comprise a container of a compound that binds to anti-*T. cruzi* antibodies and that renders said antibodies detectable.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is a description of the prior art.

FIG. 1*a*-1*h* are schematic representations of the recombinant proteins utilized in the invention.

DETAILED DESCRIPTION OF THE INVENTION

Figure 2:
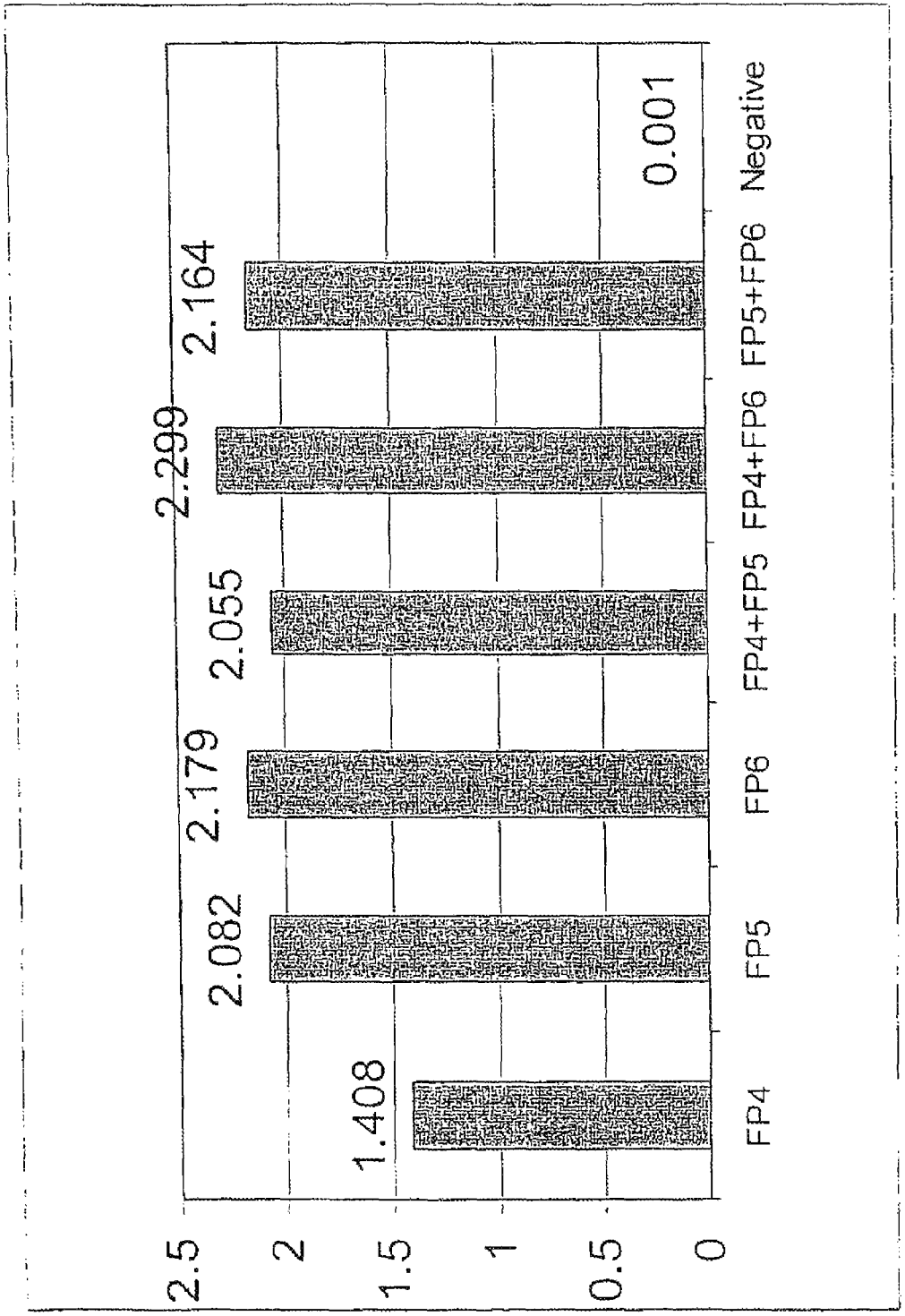
FIG. 2 is a bar graph showing reactivity of various blood specimens with recombinant proteins used alone or in combination as target antigens in ELISAs.

FIGS. 1*a*-1*h* represent the recombinant proteins of the invention, with the various letters indicating known protein sequences, as follows. The Figs. are schematic diagrams of the recombinant *T. cruzi* proteins, comprised of segments A through L. Solid segments (A, C, D, F, H, I, and K) represent nonrepetitive proteins having amino acid sequences that are unrelated to each other. Saw-tooth segments (B, E, G, J, and L) represent repetitive proteins having amino acid sequences that are unrelated to each other and unrelated to those of the nonrepetitive proteins. The relative sizes and numbers of repeats in the repetitive proteins are roughly represented in the Figs. The sizes and shapes of the nonrepetitive segments bear no relation to the actual proteins.

The following information refers to FIGS. 1 and 1*a*-1*h* in which the recombinant proteins Ag15, FP3, FP4, FP5, FP6, FP7, FP8, FP9 and FP10 are depicted schematically. These proteins are derived from *T. cruzi*, the protozoan parasite that causes Chagas disease, and are formed from of proteins A through L as indicated, and defined herein. There are no substantive amino acid similarities among proteins A through L. Similarly there are no substantive DNA sequence similarities among the segments that encode proteins A through L. The *T. cruzi* DNA sequences that encode proteins A through L were cloned in combination into pGEX and pET plasmid vectors, such as pET-32a. Strains of *Escherichia coli* were transfected with the recombinant vectors bearing the *T. cruzi* DNA sequences, and the bacteria were incubated in liquid culture under conditions favoring synthesis of the recombinant proteins. The latter proteins were subsequently affinity-purified and then used as target antigens in ELISAs. ELISAs in which proteins Ag15, FP3, FP4, FP5, FP6, FP7, FP8, FP9, and FP10, alone or in combination are employed as target antigens are useful as sensitive and specific detectors of anti-*T. cruzi* antibodies in blood specimens obtained from persons who are chronically infected with this parasite. The detection of such antibodies is the primary means of identifying persons who are chronically infected with *T. cruzi*.

The following paragraphs contain information relating to the naming, localization, and function of proteins A through L, as well as the corresponding GenBank accession numbers of the sequences to which they are related and relevant publications.

It should be noted that the *T. cruzi* gene segments that encode protein segments A through L generally are shortened versions of the native coding regions. In this context, the constructs that encode single segments (i.e., FP5 and FP9), as well as all the others that encode more than one segment, are all unique, because, even if the individual components from which the various recombinant proteins of this invention are known, the segments of the invention have not been combined previously as described herein.

Protein AB. This hybrid recombinant protein, also designated Ag15 [amino acids 218-507 of SEQ ID NO: 50] in FIG. 1, is derived from the TCR27 gene of *T. cruzi* [nucleotides 652-2151 of SEQ ID NO: 35]. Protein A is the amino terminal nonrepetitive portion of the TCR27 protein, and Protein B is comprised of approximately 18 of the 14 amino acid repeats that make up the central portion of the TCR27 protein. The two native TCR27 genes sequenced contained approximately 69 and 105 of the 14-amino acid repeats.

Nucleotide sequence data that include the Ag15 DNA sequence were deposited with GenBank and EMBL databases by Keiko Otsu, John E. Donelson, and Louis V. Kirchhoff with the accession number L04603 and are described in U.S. Pat. No. 5,876,734 and No. 6,228,601, issued to Louis V. Kirchhoff and Keiko Otsu (each of which is herein incorporated by reference in its entirety). These references also present DNA and inferred protein sequences that include the Ag15 DNA and inferred protein sequences. The Ag15 DNA and inferred protein sequences are additionally presented in Otsu K, Donelson J E, Kirchhoff L V. "Interruption of a *Trypanosoma cruzi* gene encoding a protein containing 14-amino acid repeats by targeted insertion of the neomycin phosphotransferase gene." Mol Biochem Parasitol 1993; 57:317-330, herein incorporated by reference in its entirety.

Protein C. This is a calcium binding protein of *T. cruzi*, initially called 1F8 and later designated the flagellar calcium binding protein (FCaBP) [amino acids 508-717 of SEQ ID NO: 36]. The accession number of the original 1F8 DNA sequence [nucleotides 1522-2151 of SEQ ID NO: 35] deposited in GenBank is K03278. The Protein C DNA and inferred protein sequences are presented in Gonzalez A, Lerner T J, Huecas M, Sosa-Pineda B, Nogueira N, Lizardi P M. "Apparent generation of a segmented mRNA from two separate tandem gene families in *Trypanosoma cruzi*." Nucleic Acids Res 1985; 13(16):5789-804, herein incorporated by reference in its entirety.

FIG. 1a shows a first protein (FP3) [amino acids 218-717 of SEQ ID NO: 36] in accordance with the invention. Specifically, FP3 corresponds essentially to the combination of Ag15 (FIG. 1), and by Protein C. The DNA sequence encoding FP3 [SEQ ID NO: 49], also essentially corresponds to the sequences coding for Ag15 and Protein C.

Protein D. This is the protein core of a surface glycoprotein of *T. cruzi* that is referred to as GP72 [amino acids 1-217 of SEQ ID NO: 36]. The accession number of the original gp72 DNA sequence [nucleotides 1-651 SEQ ID NO: 35] deposited in GenBank is M65021. The Protein D DNA and inferred protein sequences are presented in Cooper R, Inverso J A, Espinosa M, Nogueira N, Cross G A. "Characterization of a candidate gene for GP72, an insect stage-specific antigen of *Trypanosoma cruzi*." Mol Biochem Parasitol 1991; 49(1):45-59, herein incorporated by reference in its entirety.

FIG. 1b shows a second protein (FP4) [SEQ ID NO: 36] in accordance with the invention. The DNA sequence [SEQ ID NO: 35] that encodes Protein DABC which is a single continuous coding region, essentially corresponds to the DNA sequences from which it was constructed.

Protein E. This is a segment of the flagellar repetitive protein (FRA) of *T. cruzi* comprised of approximately nine repeats consisting of 68 amino acids each, shown as FIG. 1c (FP5) [SEQ ID NO: 38]. The accession number of the original Protein E DNA sequence [SEQ ID NO: 37] deposited in GenBank is J04015. The Protein E DNA and inferred protein sequences are presented in Lafulle J J, Linss J, Krieger M A, Souto-Padron T, de Souza W, Goldenberg S. "Structure and expression of two *Trypanosoma cruzi* genes encoding antigenic proteins bearing repetitive epitopes." Mol Biochem Parasitol 1989; 35(2):127-136, herein incorporated by reference in its entirety.

Protein FGH. This is a protein [SEQ ID NO: 40] encoded by a modified version of the *T. cruzi* TCR39 gene that was artificially constructed [SEQ ID NO: 39], shown as FIG. 1e (FP7). The modification entailed reducing the length of the central portion of the TCR39 gene that encodes the 12-amino acid repeats. Protein F is the amino terminal nonrepetitive segment of the TCR39 protein. Protein G is comprised of approximately 13 of the 12-amino acid repeats that make up the central portion of the TCR39 protein. Protein H is the carboxy terminal nonrepetitive segment of the TCR39 protein. The accession number of the original, i.e., the unmodified, Protein FGH DNA sequence deposited in GenBank is U15616. The TCR39 DNA and inferred protein sequences, which include the entire Protein FGH sequences, are presented in Gruber A, Zingales B. "*Trypanosoma cruzi*: characterization of two recombinant antigens with potential application in the diagnosis of Chagas' disease." Exp Parasitol 1993; 76(1):1-12, herein incorporated by reference in its entirety.

FIG. 1d shows another hybrid recombinant protein (FP6, Protein FGHE) [SEQ ID NO: 42] in accordance with the invention. The DNA sequence that encodes Protein FGHE [SEQ ID NO: 41], which is a single continuous coding region, essentially corresponds to the DNA sequences from which it was constructed.

Protein IJK. This is a protein [SEQ ID NO: 44] encoded by a modified version of the *T. cruzi* shed acute phase antigen (SAPA) gene that was artificially constructed [SEQ ID NO: 43], as shown in FIG. 1f (FP8). The modification entailed reducing the length of the central portion of the SAPA gene that consists of 12-amino acid repeats. Protein I is the amino terminal nonrepetitive segment of the SAPA protein. Protein J is comprised of approximately nine of the 12-amino acid repeats that make up the central portion of the SAPA protein. Protein K is the carboxy terminal nonrepetitive segment of the SAPA protein. The accession number of the original, i.e., the unmodified, Protein UK DNA sequence deposited in Gen Bank is J03985. The SAPA DNA and protein sequences, which include the entire Protein UK sequences, are presented in Affranchino J L, Pollevick G D, Frasch A C C. "The expression of the major shed *Trypanosoma cruzi* antigen results from the developmentally-regulated transcription of a small gene family." FEBS Lett 1991; 280:316-320, herein incorporated by reference in its entirety.

Protein L. This is a microtubule-associated repetitive protein (MAP) [SEQ ID NO: 46] of *T. cruzi* that is comprised of approximately five repeats consisting of 38 amino acids each, as depicted in FIG. 1g (FP9). The accession number of the original Protein L DNA sequence [SEQ ID NO: 45] deposited in GenBank is S68286. The Protein L DNA and inferred protein sequences are presented in Kerner N, Liegeard P, Levin M J, Hontebeyrie-Joskowicz M. "*Trypanosoma cruzi*: antibodies to a MAP-like protein in chronic Chagas' disease cross-react with mammalian cytoskeleton." Experimental Parasitology 1991; 73(4):451-459, herein incorporated by reference in its entirety.

FIG. 1h shows another hybrid recombinant protein (FP10, Protein UKL) [SEQ ID NO: 48] in accordance with the invention. The DNA sequence that encodes Protein IJKL [SEQ ID NO: 47], which is a single continuous coding region, essentially corresponds to the DNA sequences from which it was constructed.

Additionally, combinations of the various recombinant proteins depicted in the Figs. may be used. While it is possible to combine one or more of the recombinant proteins to form longer recombinant proteins, typically more than one recombinant protein is used simultaneously. For example, simultaneous uses of FP4 and FP5, FP5 and FP6, as well as FP4 and FP6, and combinations using more than two recombinant proteins (e.g., FP4, FP6 and FP10) are considered within the scope of the present invention. It is believed that the sensitivity and specificity of the assays according to the invention are sufficient to meet FDA standards for screening the blood supply of the United States.

Additionally, as described in U.S. Pat. No. 6,228,601 (herein incorporated by reference in its entirety), polypeptides need not correspond exactly over their entire lengths to be considered within the scope of the invention. For example, a wide variety of polypeptides which contain at least one epitope embodied in the polypeptides of the invention can be used in accordance with the present invention. Based on the nucleotide sequences, polypeptide molecules also can be produced (1) that include sequence variations, relative to the naturally-occurring sequences, (2) that have one or more amino acids truncated from the naturally-occurring sequences and variations thereof, or (3) that contain the naturally-occurring sequences and variations thereof as part of a longer sequence.

In this description, polypeptide molecules in categories (1), (2) and (3) are said to "correspond" to the amino acid sequences of the recombinant proteins of the invention. Such polypeptides also are referred to as "variants." The category of variants within the present invention includes, for example, fragments and muteins of proteins A though L, as well as larger molecules that consist essentially at least one protein sequence A through L, alone or in combination with other proteins A to L.

In this regard, a molecule that "consists essentially of" protein A to L, alone or in combination with any other proteins A to L, is one that is immunoreactive with samples from persons infected with *T. cruzi*, but that does not react with samples from patients with leishmaniasis, schistosomiasis, and other parasitic and infectious diseases, with samples from patients with autoimmune disorders and other illnesses, and with specimens from normal persons.

A "mutein" is a polypeptide that is homologous to the protein to which it corresponds, and that retains the basic functional attribute—the ability to react selectively with samples from persons infected with *T. cruzi*—of the corresponding region. For purposes of this description, "homology" between two sequences connotes a likeness short of identity indicative of a derivation of the first sequence from the second. In particular, a polypeptide is "homologous" to the corresponding protein if a comparison of amino acid sequences between the polypeptide and the corresponding region reveals an identity of greater than 40%, preferably greater than 50% and more preferably 70%. Such sequence comparisons can be performed via known algorithms, such as those described in Pearson W R, Lipman D J. "Improved tools for biological sequence comparison." Proc Natl Acad Sci USA 1988; 85(8):2444-2448, herein incorporated by reference in its entirety, which are readily implemented by computer.

A fragment of a protein of the invention is a molecule in which one or more amino acids are truncated from that protein. Muteins and fragments can be produced, in accordance with the present invention, by known de novo synthesis techniques.

Also exemplary of variants within the present invention are molecules that are longer than a protein of the invention, but that contain the region or a mutein thereof within the longer sequence. For example, a variant may include a further fusion partner in addition to the protein of the invention. Such a fusion partner may allow easier purification of recombinantly-produced polypeptides. For example, use of a glutathione-S-transferase (26 kilodaltons, GST) fusion partner allows purification of recombinant polypeptides on glutathione agarose beads.

The portion of the sequence of a such molecule other than that portion of the sequence corresponding to the region may or may not be homologous to the sequence of a protein of the invention.

It will be appreciated that polypeptides shorter than the corresponding protein of the invention but that retain the ability to react selectively with samples from persons infected with *T. cruzi* are suitable for use in the present invention. Thus, variants may be of the same length, longer than or shorter than the protein of the invention, and also include sequences in which there are amino acid substitutions of the parent sequence. These variants must retain the ability to react selectively with samples from persons infected with *T. cruzi*.

In one embodiment, the assay of the invention uses FP4 as target antigen. Table II compares the results obtained by testing 45 pre-screened Argentinean specimens in an

TABLE II

|  | | RIPA | |
|---|---|---|---|
|  | | + | − |
| FP4 ELISA | + | 9 | 0 |
|  | − | 0 | 36 |

FP4 ELISA with those obtained by RIPA testing.

The data in Table II show that in this group of specimens, the sensitivity and specificity of the FP4 ELISA were both 100%

Similarly, the performance of an FP4+FP6 ELISA in comparison to RIPA was

TABLE III

|  | | RIPA | |
|---|---|---|---|
|  | | + | − |
| FP4 + FP6 ELISA | + | 10 | 1 |
|  | − | 0 | 78 | assessed by testing 89 pre-selected Guatemalan specimens.

The data shown in Table III indicate that in this group of samples, the sensitivity of the FP4+FP6 ELISA was 100% and the specificity was 98.7%.

As shown in FIG. 2, in a FP4+FP6 ELISA, performed using standard procedures, a group of previously characterized RIPA-positive samples from several Chagas-endemic countries gave a mean reactivity (absorbance) of 2.99. Thus FP4+FP6 is the preferred embodiment among the recombinant proteins tested alone and in combination in that experiment.

It should be apparent that embodiments other than those specifically described above may come within the spirit and scope of the present invention, such as recombinant proteins comprised of different combinations and/or spatial arrangements of proteins A to L. Hence, the present invention is not limited by the above description.

We claim:

1. A recombinant polypeptide comprising a sequence having at least 70% identity to FP6 [SEQ ID NO: 42].

2. A kit comprising:
a first recombinant polypeptide wherein the first recombinant polypeptide is the recombinant polypeptide of claim 1, and
a second recombinant polypeptide.

3. The kit of claim 2, wherein the second polypeptide comprises a sequence having at least 70% identity to one selected from the group consisting of Ag15 [-amino acids 218-507 of SEQ ID NO: 50], FP3 [amino acids 218-717 of SEQ ID NO: 36], FP4 [SEQ ID NO: 36], FP5 [SEQ ID NO: 38], FP7 [SEQ ID NO: 40], FP8 [SEQ ID NO: 44], FP9 [SEQ ID NO: 46], and FP10 [SEQ ID NO: 48], wherein the first recombinant polypeptide is different from the second recombinant polypeptide.

4. The kit of claim 2, wherein the first recombinant polypeptide is FP6 [SEQ ID NO: 42] and the second recombinant polypeptide is FP4 [SEQ ID NO: 36].

5. The kit of claim 2, further comprising a third recombinant polypeptide selected from the group consisting of Ag15 [-amino acids 218-507 of SEQ ID NO: 50], FP3 [-amino acids 218-717 of SEQ ID NO: 36], FP4 [SEQ ID NO: 36], FP5 [SEQ ID NO: 38], FP7 [SEQ ID NO: 40], FP8 [SEQ ID NO: 44], FP9 [SEQ ID NO: 46], and FP10 [SEQ ID NO: 48], wherein the first recombinant polypeptide, the second recombinant polypeptide and the third recombinant polypeptide are different.

6. The kit of claim 5, wherein the first recombinant polypeptide comprises at least 70% identity to FP6 [SEQ ID NO: 42], the second recombinant polypeptide comprises at least 70% identity to FP4 [SEQ ID NO: 36] and the third polypeptide comprises at least 70% identity to FP10 [SEQ ID NO: 48].

7. A method of detecting the presence of anti-*Trypanosoma cruzi* antibodies in a sample from a subject, comprising:
(A) contacting the sample with a polypeptide comprising an amino acid sequence having at least 70% identity to FP6 [SEQ ID NO: 42] and
(B) detecting a specific binding interaction with an antibody in said sample, wherein the binding interaction comprises a specific binding between antibody in the sample and an epitope contained within the amino acid sequence having at least 70% identity to FP6 [SEQ ID NO: 42] and wherein said specific binding interaction indicates past or present infection with *Trypanosoma cruzi*.

8. The method of claim 7, wherein the polypeptide of step A is immobilized on a carrier molecule or a solid phase.

9. The method of claim 7, wherein the polypeptide of step A has a sequence obtained from a strain or clone of *Trypanosoma cruzi*.

10. The method of claim 7, wherein the polypeptide has had one or more amino acids truncated.

11. The method of claim 7, wherein the step of detecting anti-*Trypanosoma cruzi* antibodies bound to the immobilized polypeptide is carried out by adding at least one compound that detects the antibodies.

12. The method of claim 11, wherein the at least one compound that enables detection of the anti-*Trypanosoma cruzi* antibodies is selected from the group consisting of a colorimetric agent, a fluorescent agent, a chemiluminescent agent and a radionucleotide.

* * * * *